US007374875B2

(12) United States Patent  
Vita et al.

(10) Patent No.: US 7,374,875 B2  
(45) Date of Patent: May 20, 2008

(54) PEPTIDES HAVING AFFINITY FOR THE GP120 VIRAL PROTEIN AND USE THEREOF

(75) Inventors: Claudio Vita, Gif sur Yvette (FR); Loic Martin, Gif sur Yvette (FR); Christian Roumestand, Juvignac (FR); Francisco Veas, Maugio (FR)

(73) Assignee: Commissariat a l'Energie Atomique, Paris (FR)

( * ) Notice: Subject to any disclaimer, the term of this patent is extended or adjusted under 35 U.S.C. 154(b) by 569 days.

(21) Appl. No.: 10/466,835

(22) PCT Filed: Jan. 21, 2002

(86) PCT No.: PCT/FR02/00227

§ 371 (c)(1),  
(2), (4) Date: Jul. 22, 2003

(87) PCT Pub. No.: WO02/059146

PCT Pub. Date: Aug. 1, 2002

(65) Prior Publication Data

US 2006/0121538 A1 Jun. 8, 2006

(30) Foreign Application Priority Data

Jan. 23, 2001 (FR) .................................. 01 00893

(51) Int. Cl.  
*C07K 14/73* (2006.01)  
*C07K 14/435* (2006.01)  
*C12Q 1/70* (2006.01)  
*C12N 7/00* (2006.01)  
*G01N 33/569* (2006.01)  
*A61K 51/00* (2006.01)  
*A61K 38/17* (2006.01)

(52) U.S. Cl. ..................... 435/5; 424/1.17; 435/235.1; 435/7.23; 530/326; 530/324; 530/333

(58) Field of Classification Search ..................... None  
See application file for complete search history.

(56) References Cited

U.S. PATENT DOCUMENTS 4,684,622 A 8/1987 Huffman et al.  
4,721,704 A 1/1988 Chang et al.

OTHER PUBLICATIONS

Vita, et al. "Rational Engineering of a miniprotein that reproduces the core of the CD4 site interacting with the HIV-1 envelope glycoprotein" PNAS Nov. 9, 1999 vol. 96(23):13091-13096.*  
Vita, et al. Peptides 2000, Proceedings of the European Peptide Symposium, 26th, Montpellier, France, Sep. 10-15, 2000 (2001), Meeting Date 2000, 443-444. Editor(s): Martinez, Jean; Fehrentz, Jean-Alain. Editions EDK: Paris, Fr.*  
Hruby VJ and Bonner GG, "Design of Novel Synthetic Peptides Including Cyclic Conformationally and Topographically Constrained Analogs" in Methods in Molecular Biology: 35, Peptide Synthesis Protocols, Ed.: Pennington MW and Dunn BM, Humana Press: Totowa, NJ, (1994).*  
L. Martin et al.: "Engineering novel bioactive mini-proteins on natural scaffolds" Tetrahedron, vol. 56, No. 48, pp. 9451-9460 Nov. 24, 2000.  
Claudio Vita et al.: "Rational engineering of a miniprotein that reporduces the core of the CD4 site interacting with HIV-1 envelope glycoprotein" Proceedings of the National Academy of Sciences of the United States, vol. 96, No. 23, pp. 13091-13096, Nov. 9, 1999.  
P.D. Kwong et al. Nature, vol. 393, pp. 648-659 1998.  
R.W. Sweet et al. Curr. Opin. Biotechnol., vol. 2, pp. 622-633, 1991.  
S.E. Ryu et al. Structure, vol. 2, pp. 59-74, 1994.  
Y. Feng et al. Science, vol. 272, pp. 872-877, 1996.  
H. Choe et al. Cell, vol. 85, pp. 1135-1148, 1996.  
T. Dragic et al. Nature, vol. 381, pp. 667-673, 1996.  
G. Alkhatib et al. Science, vol. 272, pp. 1955-1958, 1996.  
L. Wu et al. Nature, vol. 384, pp. 179-183, 1996.  
A. Trkola et al. Nature, vol. 384, pp. 184-187, 1996.  
M. Thali et al. J. Virol., vol. 67, pp. 3978-3988, 1993.  
R. Wyatt et al. J. Virol., vol. 69, pp. 5723-2733, 1993.  
J. Moore et al. J. Virol., vol. 70, pp. 1863-1872, 1996.  
S. Chen et al. Proc. Natl. Acad. Sci., USA, vol. 89, pp. 5872-5876, 1992.  
X. Zhang et al. Nature Biotechnol., vol. 15, pp. 150-154, 1997.  
J.P. Moore et al. Perspect. Drug Disc. Design, vol. 1, pp. 235-250, 1993.  
G.P. Allaway et al. Aids Res Hum Retroviruses, vol. 11, pp. 533-539, 1995.  
M. Ono et al. Nat. Biotechnol., vol. 15, pp. 343-348 1997.  
J.O. Ojwang et al Antimicrob. Agents Chemother., vol. 39, pp. 2426-2435, 1995.  
S. Rusconi et al. Antimicrob. Agents Chemother., vol. 40, pp. 234-236, 1996.  
E. De Clercq Pure Appl. Chem., vol. 70, pp. 567-577, 1988.  
N. Yahi et al. Proc. Natl. Acad. Sci. USA, vol. 92, pp. 4867-4871, 1995.  
E. De Clercq et al. Antimicrob. Agents Chemother., vol. 38, pp. 668-674, 1994.  
O.M.Z. Howard et al. J. Med. Chem., 41, pp. 2184-2193, 1998.  
H. Tamamura et al. Biophys. Res. Commun., vol. 205, pp. 1729-1735, 1994.  
H. Tamamura et al. Bioorg. Med. Chem. Lett., vol. 10, pp. 2633-2637, 2000.  
M. Baba et al. Proc. Natl. Acad. Sci. USA, vol. 96, pp. 5698-5703, 1999.  
C. Wild et al. Proc. Natl. Acad. Sci. USA, vol. 91, pp. 12676-12680, 1994.  
L.T. Rimsky et al. J. Virol., vol. 72, pp. 986-993, 1998.  
T.W. Chun et al. Proc. Natl. Acad. Sci. USA, vol. 96, pp. 10958-10961, 1998.  
R.A. Lacasse et al. Science, vol. 283, pp. 357-362, 1999.

(Continued)

*Primary Examiner*—Mary E. Mosher  
*Assistant Examiner*—Stuart W. Snyder  
(74) *Attorney, Agent, or Firm*—Oblon, Spivak, McClelland, Maier & Neustadt, P.C.

(57) ABSTRACT

The present invention relates to a family of peptides exhibiting high affinity and specificity for the viral protein gp120, to methods for producing these peptides, and to the use of these peptides.

17 Claims, 6 Drawing Sheets

OTHER PUBLICATIONS

A. Devico et al. Virology, vol. 218, pp. 258-263, 1996.
TR Fouts et al. J. Virol., vol. 74, pp. 11427-11436, 2000.
J.L. Rossio et al. J. Virol., vol. 72, pp. 7992-8001, 1998.
S. Lee et al. J. Virol., vol. 71, pp. 6037-6043, 1997.
H. Wu et al. Proc. Natl. Acad. Sci. USA, vol. 93, pp. 15030-15035, 1996.
J.B. McMahon et al. J. Biomol. Screen, vol. 5, pp. 169-176, 2000.
J.R. Sportsman et al. Drug Discov Today, vol. 1, pp. 27-32, 2000.
C. Pernelle et al. Biochemistry, vol. 32, No. 43, pp. 11682-11687, 1993.
G. Mathis Clin. Chem., vol. 39, No. 9, pp. 1953-1959, 1993.

* cited by examiner

─✕─ gp120+CD4M27    ─▫─ gp120+CD4M9    ─△─ gp120+(A23)CD4M9
─●─ gp120 alone      ─── gp120+CD4s

```
                    Q I K I L G N Q G S F L T K G P   sCDA
                    33              40          48   (CDR2)

Z F T N V S C T T S K E C W S V C Q R L H N T S R G K C M N K K C R C Y S   ChTx
1              10              20              30              37

- - - V S C T T S K E C W S V C Q R L H N T S K G G C Q G S F C T C G P    CD4K
                                                                31

A F C N L R M C Q L S C R S L G L L G K C I G D K C E C V K H              scTx
      1

PEPTIDES HAVING AFFINITY FOR THE GP120 VIRAL PROTEIN AND USE THEREOF

TECHNICAL FIELD

The present invention relates to a family of peptides exhibiting high affinity and specificity for the viral protein gp120, to methods for producing these peptides, and to the use of these peptides.

The viral protein gp120 is a glycoprotein of the envelope of the immunodeficiency virus. It is involved in the first step of the replication cycle of the virus, i.e. in the step consisting of recognition of the CD4 protein of the lymphocyte membrane by the envelope of the virus, and of fusion of the membranes so as to internalize the nucleocapsid. It is in fact the outermost protein of the site for recognition of the CD4 protein by the envelope of the virus.

Many immunodeficiency viruses exist which comprise an envelope protein similar to the viral protein gp120. Among these, mention may be made of the human immunodeficiency virus (HIV), the simian immunodeficiency virus (SIV), the ovine immunodeficiency virus (VISNA), the bovine immunodeficiency virus (BIV) and the feline immunodeficiency virus (FIV).

Some peptides of the present invention are capable of attaching to the viral protein gp120 of the viral envelope, and of inhibiting the attachment of the viral protein gp120 to the CD4 receptor, with $IC_{50}$ values of between 0.1 and 400 nM depending on their sequence. Some of these molecules are capable of inhibiting T lymphocyte infection with the HIV virus, with, for example, an $ED_{50}$ (50% effective dose) of 100 to 900 nM. In addition, the attachment of these molecules to recombinant viral protein gp120 induces a conformational variation therein which unmasks new epitopes, with the same effectiveness as the soluble CD4 molecule.

The peptides of the present invention can find therapeutic and vaccine applications. They also make it possible to design novel molecules which are of use, for example, in the detection, and also in the purification, of the envelope protein of HIV and in the discovery of new anti-AIDS drugs.

PRIOR ART

Many studies are being carried out in order to find effective treatments for and means of preventing infection with immunodeficiency virus, and in particular the human immunodeficiency virus (HIV). The major difficulties concern the development of vaccines and of immunotherapeutic treatments which are effective. This is due, in particular, to the variability of the virus, and to the difficulty in understanding the mechanism of its entry into target cells and of the immune response required in order to protect against infection by the virus.

In the following description, the references between square brackets refer to the documents in the attached list of references.

As demonstrated by analysis of the three-dimensional structure of the CD4-gp120 complex [1] (see attached references), the structural elements of CD4 which are essential for its binding to the viral glycoprotein gp120 include the amino acids Gly38, Gln40, Gly41, Ser42, Phe43 and Thr45, which are included in region 36-47, and arginine-59 of CD4. Region 36-47 of CD4 has been compared to the CDR2 region of immunoglobulins and exhibits an ordered hairpin structure. This structure is made up of a β-strand (C'), corresponding to sequence 36-40, followed by a turn corresponding to sequence 40-43 which allows a second β-strand (C"), corresponding to sequence 43-47, to form, with the first, an anti-parallel β-structure. This structure is stabilized by hydrogen bonds between the amide nitrogen of the residues Gly38, Gln40, Phe43, Thr45 and Gly47 of the first β-strand and the carbonyl oxygen of the residues Thr45, Phe43, Gln40, Gly38 and Ile36, respectively, of the second β-strand. This hairpin structure has a central role in the interaction of CD4 with the viral protein gp120 and performs a double function. Firstly, it allows the amino acids Gly38, Gln40, Gly41, Ser42, Phe43 and Thr45 to form a molecular surface complementary to the surface of interaction of the viral protein gp120 and, in particular, enables the side chain of Phe43 to insert into the entrance of a hydrophobic cavity in the molecular surface of the viral protein gp120; secondly, it allows an interaction of the β-sheet type between the polypeptide backbones of the β-strand C" of CD4 and the β15 strand (residues 365-368) of the viral protein gp120. The arginine 59 (Arg59) also has an essential role in the CD4-gp120 interaction, since the guanidinium group of its side chain forms a double hydrogen bridge with the side chain of the residue Asp368 of the viral protein gp120, allowing stabilization of the β-structure-type interaction between the C" strand of CD4 and the β15 strand of the viral protein gp120. Site-directed mutagenesis experiments have demonstrated that all these residues of CD4 play an essential role in the interaction with the viral protein gp120 [2], [3].

Reproduction of this ordered hairpin structure and of the conformation of the side chains of its residues is essential in a molecule which must attach to the viral protein gp120 at the site of interaction of CD4. The fact that simple peptide constructs, such as a linear peptide corresponding to sequence 37-53 and a cyclic peptide corresponding to sequence 37-46 of CD4, do not possess measurable affinity for the viral protein gp120 is a demonstration of this [4].

CD4 cell infection with HIV is mediated by a high affinity interaction between the viral envelope and CD4. Experiments consisting of mutageneses and of competition with antibodies have made it possible to locate the surface of contact with the gp120 protein of the viral envelope, in domain D1 of CD4. The three-dimensional structure of a recombinant form of the gp120 glycoprotein which is functional but deleted of loops V1-V2-V3 and of the N- and C-terminal regions, in a complex with domains D1D2 of CD4 and with the Fab fragment of a monoclonal antibody, has recently been resolved by crystallography [1]. In this structure, the CD4 interacts with a large depression at the molecular surface (800 $Å^2$) of the viral protein gp120, using a large molecular surface (742 $Å^2$), which is centred around the region which has been compared to the CDR2 region of immunoglobulins. A narrow and deep cavity opens up at the centre of the molecular depression of the viral protein gp120, called the "Phe43 cavity", the entrance to which is occupied by the side chain of Phe43, at the top of the CDR2 region of CD4. The resolution of this structure confirms the preceding data for mutagenesis, which indicates that the residue Phe43 and the entire CDR2 loop are functionally very important, and proposes the latter as a possible target for inhibiting the attachment of HIV-1 virions to cells. The gp120-CD4 interaction allows the virus to attach to the membrane of the target cells and represents the first protein-protein interaction in the infection mechanism. However, other co-receptors are required for effective entry of HIV into cells. These are CXCR-4 [5], [6], which is involved in the entry of lymphotrophic viral strains (×4), and CCR-5 [7], [8], which is involved in the entry of M-tropic strains (R5)

and of most primary isolates. Several pieces of proof indicate that the attachment of the viral protein gp120 to CD4 would produce conformational variations in the envelope glycoprotein, which would expose new sites, detectable by specific antibodies, called CD4i, and would increase the affinity of the envelope for the chemokine receptors [9], [10], the co-receptors for entry. After attachment of CD4 and of the co-receptor by the viral protein gp120, other conformational variations would lead to a structural reorganization of gp41, which would result in exposure of its fusogenic peptide, then to fusion of the viral and cellular membranes and, finally, to entry of the viral load into the cell.

The crystallographic structure of the viral protein gp120 forming a complex with CD4 has made it possible to elucidate one of the mechanisms used by HIV to invade the immune response. It was already known that the gp120 envelope protein has hypervariable and strangely glycosylated regions. The crystallographic structure in fact demonstrates that the hypervariable regions and the highly glycosylated regions form the exposed molecular surface of the viral protein gp120, which also corresponds to the accessible surface of the virions. Only a few regions of the molecular surface of the viral protein gp120 are conserved and can be the target for antibodies. These regions are not normally accessible and are probably protected by the hypervariable loops (V1-V2-V3) which, in the crystallized protein, have been deleted and are therefore invisible. One of these regions is a surface close to the site of interaction for chemokine receptors, and accessible to the CD4i antibodies, after attachment of the envelope to CD4. The CD4-binding site is another exposed and conserved surface: however, this surface is present in a cavity of the viral protein gp120 and is not therefore accessible to antibodies, but can accommodate CD4, which has a single immunoglobulin domain, unlike antibodies, which use two domains for molecular recognition.

The tools available today for recognizing the envelope protein (gp120) are limited. These are the CD4i antibodies [11], [12], [13], which are capable of attaching a broad spectrum of primary envelopes; however, their affinity for the viral envelope is low and only increases in the presence of CD4, which means that they cannot be readily used with ease. Other antibodies, such as IgG1b12, F105 or 15e, are not thought to be capable of recognizing all primary isolates. A CD4 molecule labelled with biotin might also represent a solution. This molecule is commercially available (Intracel). Unfortunately, it is expensive and its functional properties of attachment of the viral protein gp120 have been greatly decreased (100-fold) by the biotinylation reaction, which greatly limits its use.

Inhibition of the interaction of the viral protein gp120 with the main receptor for entry, CD4, with a recombinant soluble CD4 and/or with immunoglobulin chimeras containing CD4 domains was one of the first therapeutic approaches suggested and experimentally investigated for inhibiting infection with HIV-1. These molecules are effective in vitro in the inhibition of viral infection only in the case of laboratory-adapted strains, but are ineffective in the case of many primary isolates. The rapid degradation in vivo of these CD4-derived constructs and their lower affinity for the viral envelope of primary isolates have been proposed as main causes of their ineffectiveness. However, studies have demonstrated that the affinity, for CD4, of recombinant monomeric gp120s of certain primary isolates is not significantly different from that of gp120s derived from laboratory strains. The oligomeric nature of the viral protein gp120 at the viral surface, the density and structure of CD4 at the surface of the permissive cells and can be the presence of other molecular interactions not yet clearly elucidated or of other secondary molecules for entry might play an important role in the mechanism of entry and represent other causes of the ineffectiveness of the soluble CD4 proteins as entry antagonists. The development of antiviral agents which target the viral protein gp120 presents a major challenge, due to the great genetic variability of the envelope protein, a factor which may explain the ineffectiveness of many inhibitors of the viral protein gp120. However, the fact that the residues which contribute to forming the core of the binding site of the viral protein gp120 for CD4 are made up of very conserved residues suggests that inhibitors of the viral protein gp120 may be effective against a broad spectrum of HIV-1 isolates.

CD4-derived peptide constructs have been proposed as inhibitors of the viral infection: they are a structural mimetic peptide of the CDR2 loop of CD4 which incorporates a phenyl group which mimics the Phe43 [14] and a cyclic peptide corresponding to the CDR3 loop of CD4 and incorporating additional aromatic residues [15]. However, these constructs exhibit low antiviral activity limited to a laboratory isolate and, even though they were initially designed as structural mimetics of CD4, they are not active in the entry step [16].

Currently, a certain number of inhibitors of the gp120-CD4 interaction have been proposed and have a clinical application. They are, for example, a large recombinant protein formed by the genetic fusion of the D1D2 domains of CD4 with the constant domains of an IgG2 immunoglobulin [17]. This construct PRO542 is in clinical phase I/II. This large recombinant protein appears to be well tolerated by the human body, but its effectiveness depends on a high circulating dose which is difficult to achieve. Smaller molecules have been proposed as inhibitors of the CD4-gp120 interaction and are in the clinical test phase. They are: a bisazo dye FP21399 [18], identified by a combinatorial approach, the phosphorothioate oligonucleotide zintevir (AR177) [19], a naphthalenesulphonate-based polymer, PRO2000 [20] and a starch derivative, dextrin 2-sulphate (D2S) [21], which inhibit HIV-1 chemical isolates in cell cultures, but require high concentrations. Among the entry inhibitors, there is also SPC3 [22], a multibranched synthetic peptide construct which, initially proposed as an inhibitor of the CD4-gp120 interaction, then proved to be active in a step following virion attachment to the cells. Other small molecules have been proposed as entry inhibitors: bicyclam AMD3100 [23], NSC651016 [24], the peptide T22 [25], and its more recent version T134 or T140 [26], and TAK779 [27]. These molecules are inhibitors of viral entry which are active on the co-receptors for entry CXCR4 and CCR5, but which have no activity in the CD4-gp120 interaction. Peptides derived from the sequence of the C-terminal region of the gp41 glycoprotein, the peptide T20 (or DP178) [28] and its more recent improved version DT1249 [29] are other inhibitors of the infection which target a transient phase of entry, subsequent to attachment of the viral envelope to CD4 and preceding the virus cell membrane fusion: these peptides are inactive in the gp120-CD4 interaction. Most of these products are currently in clinical test phase I/II, but their therapeutic effectiveness still remains to be verified.

The anti-AIDS therapeutic regime currently used clinically, tritherapy, comprises a combination of three inhibitors which target two viral enzymes, reverse transcriptase and protease. Even though tritherapy has succeeded in significantly reducing the viral load of many patients, it is not capable, even in the most favourable cases, of eradicating the disease, since dormant reservoirs of infection still persist [30]. The partial success of tritherapy, on the one hand, and the impossibility of stopping the AIDS infection with the current therapeutic protocols, on the other hand, have increased the demand for new drugs which may be active on other viral targets and which can increase the repertoire and effectiveness of the current clinical drugs.

Experiments in the laboratory of J. H. Nunberg, Montana Biotechnology Center, The University of Montana, Missoula, USA, have demonstrated that the chemical bridging of protein forms present in the step preceding virus-cell fusion represents new immunogens which are capable of inducing the formation of virus-neutralizing antibodies [31]. The pre-fusion complex of the viral envelope with the entry receptors therefore represents a structure currently of great interest, because this structure might represent the most important component of a protein formation in the preparation of a vaccine against AIDS. Experiments in the laboratory of A. DeVico, Institute of Human Virology, University of Maryland, Baltimore, USA, have demonstrated that the gp120-CD4 complex, stabilized by chemical bridging or as a recombinant fusion protein, represents a macromolecular form which exposes cryptic antigenic sites of the viral protein gp120 and which is capable of inducing neutralizing antibodies [32], [33]. Obtaining this antigenic complex by chemical bridging is not satisfactory since it is not homogeneous and difficult to reproduce. Obtaining it as a recombinant protein does not result in a structurally stable and effective form. However, especially, the presence of CD4 in these preparations might pose the danger of inducing an autoimmune response in an organism which is already immunosuppressed.

Furthermore, production of the viral envelope in its recombinant monomeric form (gp120) or in the more native trimeric form (gp140 or analogues) is of very great value in searching for and in the large-scale production of recombinant forms which can potentially be used for vaccination. The purification of these recombinant forms is not easy and involves the use of chromatographic supports functionalized with ligands, especially lectins, which are not very specific for the envelope protein. The use of a chromatographic support containing the recombinant CD4 covalently attached would introduce a step which is more specific and effective for purifying the viral protein gp120, but such a support would be very expensive and this protein would not be sufficiently stable under all conditions of use.

Explanation of the Invention

The present invention provides a family of peptides which mimic CD4 and overcome the abovementioned drawbacks of the prior art. Specifically, it provides a stable peptide exhibiting very high affinity for the envelope of the AIDS virus, in particular for the gp120 protein.

The peptide of the present invention is characterized in that it comprises the following sequence (A):

TPA-P$^1$-Cys-P$^2$-Cys-P$^3$-Cys-(Ala or Gln)-(Gly or (D)Asp or Ser)-(Ser or His or Asn)-Xaa$^j$-Cys-(Thr or Ala)-Cys-Xaa$^k$-NH$_2$ in which TPA represents thiopropionic acid, Xaa$^j$ represents β-naphthylalanine, phenylalanine or diphenylalanine, Xaa$^k$ represents Gly, Val or Ile, P$^1$ represents 3 to 6 amino acids, P$^2$ represents 2 to 4 amino acids and P$^3$ represents 6 to 10 amino acids, the amino acids in P$^1$, P$^2$ and P$^3$ being natural or unnatural, identical or different, and P$^1$, P$^2$ and P$^3$ possibly having a common sequence, said peptide exhibiting a β-hairpin conformation in which the β-turn is formed by the amino acid residues (Ala or Gln)-(Gly or (D)Asp or Ser)-(Ser or His or Asn)-Xaa$^j$ of its sequence (A).

According to one embodiment of the present invention, the peptide of the present invention is characterized in that it comprises the following sequence (I):

```
TPA-Xaa^a-Xaa^b-Ala or Gln or His-Arg or Phe-
  1                                          5

Cys-Xaa^c-Xaa^d-Arg-Cys-Lys-Xaa^e-Xaa^f-
                    10

Xaa^g-Xaa^h-Leu or Lys-Xaa^i-Lys-Cys-Ala
       15 or Gln-Gly or (D)Asp or Ser-Ser or His or Asn-
20

Xaa^j-Cys-Thr or Ala-Cys-Xaa^k-NH2,
          25
``` in which TPA represents thiopropionic acid, Xaa$^a$, Xaa$^b$, Xaa$^c$, Xaa$^d$, Xaa$^e$, Xaa$^f$, Xaa$^g$, Xaa$^h$ and Xaa$^i$ are natural or unnatural, identical or different amino acids, Xaa$^j$ represents Nal, Phe or Dip, and Xaa$^k$ represents Gly, Val or Ile.

The residue (D)Asp represents the D optical isomer of aspartic acid, Nal represents β-naphthylalanine and Dip represents diphenylalanine.

The inventors demonstrated that the peptide of the present invention defined by sequence (I), comprising a thiopropionic acid at position 1 of the sequence, a Phe, Nal or Dip residue at position 23 of the sequence (Xaa$^j$) and a Gly, Val or Ile residue at position 27 of the sequence (Xaa$^k$), exhibits high affinity and great binding specificity for the gp120 protein of the viral envelope of the immunodeficiency virus.

This peptide comprises only 27 or 28 residues, and has a hairpin structure consisting of two antiparallel β strands linked by a β-turn of four residues. The two antiparallel strands, since they are at a distance from one another which can give intramolecular hydrogen bridge interactions, stabilize the structure. In particular, the distance between the amide nitrogen and carbonyl oxygen atoms of the peptide bond is 2.5 to 3.6 Å. This well-defined and stable structure reproduces structural elements of CD4 which are essential for its binding to the gp120 glycoprotein.

The three-dimensional structure of the peptide of the present invention has been experimentally resolved by nuclear magnetic resonance (NMR). This analysis demonstrates that the three-dimensional organization of this peptide reproduces the peptide backbone of the hairpin structure of CD4, and region 37-46 of this peptide can be superimposed on region 36-37 of CD4 with an rms deviation of only 1.05 Å. In addition, the side chains of the residues Ala or Gln 20, Ser 22, Xaa$^j$ 23 (Nal, Phe or Dip), and Thr or Ala 25 have an orientation comparable to that of the corresponding residues of CD4, namely Gln 40, Ser 42, Phe 43 and Thr 45. In particular, the side chain of Xaa$^j$ 23 protrudes from the hairpin motif in a conformation similar to that of the Phe 43 of CD4 so as to insert into the entrance of a hydrophobic cavity of the viral protein gp120, thus reinforcing the link with gp120. Arg and Lys at positions 9 and 18 are topologically equivalent to the residues Arg59 and Lys35 of the CD4 protein.

TPA and the 5 cys of the peptide form disulphide bridges which exhibit pairing of the 1-3, 2-4 and 3-6 type and stabilize the hairpin structure.

The hairpin structural motif has a surface accessible to the solvent and/or to a larger molecule such as a protein, which can promote its interaction with the viral envelope protein.

The side chains of the amino acids of the solvent-accessible surface of this motif are spatially close and form a continuous molecular surface which reproduces the structure of several residues which are important for CD4-gp120 binding.

The structural platform which contains the hairpin structural motif also contains other structural regions capable of accepting additional chemical functionalities in a spatial position which is well defined relative to the hairpin structural motif, which may thus reinforce its biological function of binding and/or provide labelling groups. For example, a biotin group or a fluorescein group has been incorporated into the side chain of lysine 11, without causing any loss in biological activity of the derivative. Incorporation of these groups has made it possible to use these derivatives in assays for interaction with the envelope protein, as described below.

According to the invention, sequence (I) may also comprise a proline residue linked to the residue $Xaa^k$. A proline residue added at position 28 stabilizes the C-terminal end and makes the C-terminal β-strand of the hairpin structural motif less flexible.

According to the invention, in sequence (I), $Xaa^i$ may be Gly.

For example, the peptide of the present invention may comprise a sequence chosen from sequences ID No. 4, ID No. 5, ID No. 6, ID No. 7, ID No. 8, ID No. 9, ID No. 10, ID No. 11, ID No. 12, ID No. 13, ID No. 14, ID No. 15 and ID No. 16 of the attached sequence listing.

The peptide of the present invention can be obtained by solid-phase chemical synthesis or by genetic recombination. Thus, the present invention also relates to a method for producing the peptide according to the invention as defined above, said method comprising solid-phase chemical synthesis of said peptide. The chemical synthesis can be carried out, for example, with an automatic peptide synthesizer of the Applied Biosystems, mod. 433A type. It can be carried out, for example, by Fmoc chemistry which uses the fluorenylmethyloxycarbonyl group for temporary protection of the α-amino function of the amino acids.

The peptide of the invention can also be produced by means of a method comprising the following steps:
a) integrating a nucleic acid sequence into an expression vector, said nucleic acid sequence encoding the peptide of the present invention,
b) introducing the expression vector comprising said nucleic acid sequence into a host cell,
c) culturing the host cell comprising said nucleic acid under culture conditions which allow the synthesis of said peptide,
d) recovering the synthesized peptide, and
e) grafting TPA at the C-terminal position.

The technical elements for carrying out this method of peptide synthesis are known to those skilled in the art. They are described, for example, in the work by Sambrook, Fritsch and Maniatis, MOLECULAR CLONING, A LABORATORY MANUAL, 2nd edition. The grafting of a TPA at the N-terminal position of the peptide can be carried out by means of a conventional method of organic chemistry applicable to a peptide.

The inventors have synthesized a family of peptides reproducing a portion of the structure of the region of CD4 resembling the CDR2 region of immunoglobulins, which, as demonstrated by the mutagenesis and crystallographic analysis results, are among the regions essential for CD4 binding to the viral protein gp120. The peptides of the present invention are capable of attaching to the region of the gp120 glycoprotein which interacts with CD4, the main receptor for HIV-1 entry into CD4 target cells.

They constitute a family of inhibitors, the affinity of which for recombinant monomeric viral glycoprotein gp120 varies between $IC_{50}$ values ranging from 0.1 nM to 400 nM. They represent specific and powerful inhibitors of the CD4-gp120 interaction which are based on the structure of CD4. The binding with the recombinant viral protein gp120 occurs in competition with soluble CD4 and is specific for the correctly structured form.

Due to the structure and functional mimicking of CD4, these peptides can be used in the various fields described below.

The peptides of the present invention can attach the HIV-1 envelope in its recombinant form as demonstrated by the ELISA assays. These peptides, after labelling with a suitable fluorescent or radioactive probe, make it possible to detect the presence of the HIV-1 envelope in solution or at the surface of a cell, and therefore to detect the presence of an infected cell and therefore of the HIV-1 infection.

The peptides of the present invention inhibit the interaction between the recombinant CD4-gp120 proteins in vitro and, through this, they are also capable of stopping entry of the HIV-$1_{LAI}$ virus (primary isolate) and HIV-$1_{LEN}$ virus (clinical isolate) into circulating lymphocytes. The most powerful peptides of the present invention are, in fact, capable of inhibiting lymphocyte infection with an $ED_{50}$ of between 100 and 900 nM. These molecules therefore represent antiviral agents which find a clinical application. Due to their peptide nature, they can be used by injection or infusion, or in external local applications.

The ability of the peptides of the present invention to inhibit binding of the viral protein gp120 to CD4 is a demonstration of the ability of these peptides to inhibit the viral infection, since they prevent one of the first steps of the viral entry. These entry inhibitors are therefore components with antiviral action. The peptides of the present invention therefore represent molecules which can be used in anti-HIV therapy.

The peptides of the present invention are capable of inducing variations in the conformation of the recombinant viral protein gp120 and of the envelope, which make it possible to be detected by specific monoclonal antibodies, called CD4i, such as CG10, 17b and 48D. These conformational variations are therefore apparently similar to those which are induced by the binding of CD4. The binding of the peptides of the invention to the recombinant viral protein gp120 and to the viral envelope therefore unmasks envelope epitopes which are not normally accessible without CD4. These epitopes represent novel antigenic sites which are potentially very important for developing HIV-1-neutralizing antibodies. The peptides of the present invention can therefore also be used in a vaccine application, in particular in a formulation which comprises the complexing thereof with a protein of the viral envelope.

Some peptides of the present invention exhibit lower affinity for the recombinant viral gp120 protein than others. These peptides are also of very great practical use in the purification of functional forms of the viral envelope. Specifically, the attachment of the viral protein to these peptides is more readily reversible. To demonstrate this, the inventors covalently attached one of these peptides to a hydrophilic polymeric support (Sepharose 4B) used in liquid chromatography, using a flexible arm attached on the side opposite the active surface of the molecule. This molecule, attached in this way, can still interact with the recombinant viral protein gp120 and is capable of retaining this viral protein on the polymeric matrix. It can then be detached by acidification of the medium. A support thus functionalized therefore makes it possible to purify the recombinant viral protein gp120, and optionally other forms of the viral envelope and even the whole virus, in large-scale preparations.

In addition, the peptides of the present invention can be labelled, for example with fluorescein or biotin, or radiolabelled, without the affinity for binding to the viral envelope protein gp120 being altered. These labelled peptides can be used as tracers, in experiments involving competition for their binding to gp120, for example to carry out molecular screening. The methods which can be used are those which are accessible to those skilled in the art in the literature which relates to the study of molecular interactions (see, for example, [37, 38, 39 and 40]). In a screening method, any molecule capable of inhibiting the interaction between a peptide of the present invention and a gp120 viral protein may represent an inhibitor of the CD4-gp120 interaction and therefore an inhibitor of the viral infection. It is therefore possible, by virtue of the peptides of the present invention, to screen any molecule capable of interacting with the gp120 protein, or a protein analogous to gp120, in particular molecules with antiviral activity or molecules which are of use for producing a medicinal product.

The present invention therefore also relates to the use of the peptide according to the invention as defined above, for preparing a medicinal product.

It also relates to the use of the peptide according to the invention as defined above, for preparing an antiviral agent.

It also relates to the use of the peptide according to the invention as defined above, for preparing a medicinal product intended for the treatment of AIDS.

It also relates to a vaccine comprising a complex of a peptide according to the invention and an envelope protein of a virus. The virus may be an AIDS virus such as those mentioned above.

The present invention also relates to the use of the peptide according to the invention as defined above, for producing a diagnostic product, for example for diagnosing AIDS.

It also relates to the use of a peptide according to the invention as defined above, for detecting molecules of the viral envelope of HIV.

It also relates to the use of the peptide according to the invention as defined above, for screening molecules which inhibit the interaction of gp120, or of its analogues, with the CD4 molecule, for screening molecules with antiviral activity and for screening molecules which are of use for producing a medicinal product.

It also relates to the use of the peptide according to the invention as defined above, as an immobilized ligand for functionalizing a chromatography matrix.

Even more advantages will become apparent on reading the following examples with reference to the sequence listing and to the attached figures.

Brief Description of the Sequence Listing

The attached sequence listing provides the following peptide sequences:

sequence ID No. 1: sCD4 sequence.
sequence ID No. 2: sequence of scyllatoxin (ScTx).
sequence ID No. 3: CD4M9 sequence: peptide derived from scyllatoxin, exhibiting no TPA at position 1 of the sequence.
sequence ID Nos 4-16: sequences named CD4M9T, CD4M26, CD4M27, CD4M27A, CD4M27B, CD4M27C, CD4M30, CD4M31, CD4M32, CD4M33, CD4M35, K15 and K16, respectively, according to the present invention.
sequence ID No. 17: sequence named CD4M3, derived from scyllatoxin, exhibiting no TPA at position 1 of the sequence.
sequence ID No. 18: sequence named CD4MO, derived from charybdotoxin.

BRIEF DESCRIPTION OF THE FIGURES

FIG. 7: Examples of peptide sequences of the present invention represented with the one letter codes for the amino acid residues. TPA and B represent thiopropionic acid and diphenylalanine, respectively, and "d" represents the D optical form of aspartic acid. sCD4=SEQ ID NO: 1; ScTx=SEQ ID NO: 2; CD4M9=SEQ ID NO: 3; CD4M9T=SEQ ID NO: 4; CD4M27=SEQ ID NO: 6; CD4M27A=SEQ ID NO: 7; CD4M27B=SEQ ID NO: 8; CD4M27C=SEQ ID NO: 9; CD4M30=SEQ ID NO: 10; CD4M32=SEQ ID NO: 12; CD4M33=SEQ ID NO: 13; CD4M35=SEQ ID NO: 14; K15=SEQ ID NO: 15; K16=SEQ ID NO: 16; CD4M3=SEQ ID NO: 17; CD4M=SEQ ID NO: 18; chTX=SEQ ID NO: 19.

EXAMPLES

Example 1

Figure 1:
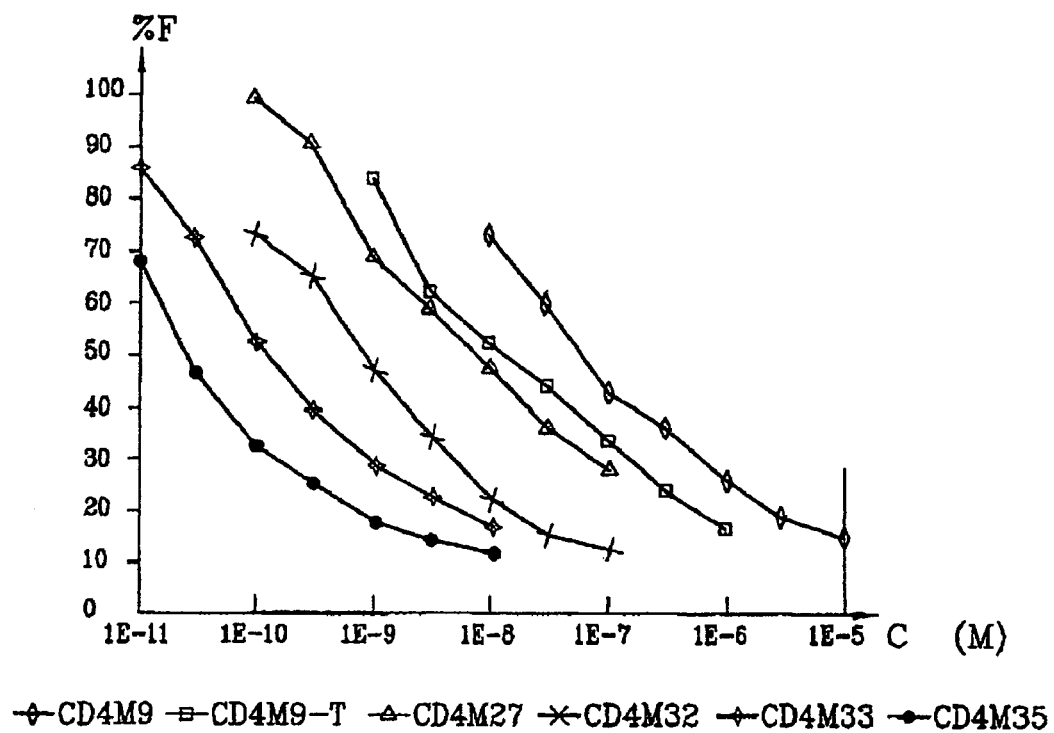
FIG. 1: Curves of inhibition of the binding of CD4 to the viral protein gp120, with peptides of the present invention, obtained by competition ELISA. The peptides tested are: CD4M9, CD4M9T, CD4M27, CD4M32, CD4M33 and CD4M35. The experimental data are given as percentage binding (% F) as a function of the peptide concentration.

Synthesis of the Peptides of the Present Invention

The peptides of the present invention were produced, in this example, by solid-phase chemical synthesis with an Applied Biosystems automatic peptide synthesizer, mod. 433A, and by Fmoc chemistry, which uses the fluorenylmethyloxycarbonyl (Fmoc) group for temporary protection of the α-amino function of the amino acids. The protective groups used to prevent the side reactions of the lateral chains of the amino acids, in this Fmoc strategy, were tert-butyl ether (tBu) for the Ser, Thr and Tyr residues; tert-butyl ester (OtBu) for Asp, Glu; trityl (Trt) for Gln, Asn, Cys, His; tert-butyloxycarbonyl (Boc) for Lys, and 2,2,5,7,8-pentamethylchromane-6-sulphonyl (Pmc) for Arg.

The coupling reaction takes place with a 10-equivalent excess of amino acids (1 mmol) relative to the resin (0.1 mmol). The protected amino acid is dissolved in 1 ml of N-methylpyrrolidone (NMP) and 1 ml of a solution of 1M 1-N-hydroxy-7-azabenzotriazole (HOAt) in the NMP solvent. 1 ml of a solution of 1M N,N'-dicyclo-hexylcarbonodiimide (DCC) is then added. After activation for 40 to 50 minutes, the active ester formed is transferred into the reactor which contains the resin. Before this step of transfer then coupling, the resin is deprotected with respect to its Fmoc group, with a solution of 20% piperidine in NMP. The excess piperidine is removed by washing with NMP after approximately 5 to 10 minutes.

During the deprotection, detection of the dibenzofulvene-piperidine adducts at 305 nm makes it possible to follow the correct progression of the synthesis. Specifically, quantification of the adduct makes it possible to estimate the effectiveness of the deprotection of the Fmoc group and, consequently, of the coupling of the final amino acid incorporated.

Chemical Modifications Incorporated into the Peptides of the Present Invention

A fluorescent probe and also a biotin group were coupled to two of the peptides of the present invention studied, CD4M9T (sequence ID No. 4) and CD4M33 (sequence ID No. 13). The incorporation onto these two compounds occurred on the residue lysine 11, on a face opposite to the site for binding of the viral protein gp120. This choice of a lysine was conditioned by its possibilities of protecting its side chain with a protective group, termed orthogonal, such as the 1-(4,4-dimethyl-2,6-dioxocyclohexylidene)ethyl group. Such a group is in fact stable with respect to the treatment with 20% piperidine used to deprotect the Fmoc group, but is specifically cleaved by treatment with a 2% hydrazine solution. Once the Dde group had been removed, it was possible to couple the fluorescein and also the biotin.

Introduction of fluorescein. The fluorescent group was introduced onto the side chain of lysine 11 of the peptide of the present invention CD4M33 and of lysine 15 or 16 of the peptide K15 (sequence ID No. 15) or K16 (sequence ID No. 16), respectively, of the present invention. The Dde group was therefore used to protect the side chain of the lysine during peptide synthesis, and was then released by two treatments for 5 min with 2% hydrazine in dimethylformamide (DMF). The fluorescein molecule was coupled directly to the synthesized peptide or via an arm, which serves to distance the fluorescein, a bulky molecule, which might hinder the binding activity. In the latter case, the molecule which enables an arm to be introduced is Fmoc-8-amino-3,6-dioxaoctanoic acid. 17 equivalents of Fmoc-8-amino-3,6-dioxaoctanoic acid, 60 equivalents of diisopropylethylamine (DIEA) and 17 equivalents of 2-(1H-benzotriazol-1-yl)-1,1,3,3-tetramethyluronium hexafluorophosphate (HBTU) are thus added to one equivalent of resin. After coupling for 1 hour at ambient temperature, the Fmoc group is deprotected with 20% piperidine. The coupling of the probe was then carried out using the N-hydroxysuccinimidyl fluorescein 5(6)-carboxylate ester. For this, 4 equivalents of activated ester of fluorescein are added to one equivalent of resin, in the presence of 14 equivalents of diisopropylethylamine (DIEA). The reaction takes place in the NMP solvent overnight. The final deprotection is finally carried out.

Introduction of biotin. An 8-amino-3,6-dioxaoctanoic spacer arm was added, in a first step, on lysine 11 deprotected beforehand with respect to the Dde group. The reaction is similar to that described in the preceding paragraph. The biotin is then incorporated in the form of an N-hydroxysuccinimidyl biotinamidocaproate ester: 4 equivalents of activated ester of biotin are thus added to one equivalent of resin, in the presence of 14 equivalents of diisopropylethylamine (DIEA). The reaction occurs overnight at ambient temperature. The resin is then washed before being treated with the final deprotection solution.

Introduction of a thiol group. The peptide CD4M9 is synthesized according to the procedure described above, with the lysine at position 11 having a Dde group as protective group for the side chain. After synthesis of the peptide, the peptide-resin is treated 5 times with a solution of 2% hydrazine in DMF. The coupling of a linker arm is carried out for one hour at ambient temperature in DMF with 10 equivalents of Fmoc-8-amino-3,6-dioxaoctanoic acid, using the reagent HBTU in the presence of diisopropylethylamine. The Fmoc group is then deprotected with 20% piperidine in DMF. The peptide-resin is consequently treated with 10 equivalents of Traut's reagent (2-iminothiolane hydrochloride (Sigma)) in the presence of DIEA. The peptide is finally released and deprotected as described below.

Final Deprotection of the Resin

Cleavage of the resin and of the protective groups present in the side chains were carried out simultaneously by treatment of the peptide linked to the resin with trifluoroacetic acid (TFA). Before performing the cleavage, the resin was washed several times with dichloromethane (DCM) and finally dried. The reagent used in the cleavage is an acid mixture containing 81.5% of TFA and the scavengers phenol (5%), thioanisole (5%), water (5%), ethanedithiol (2.5%) and triisopropylsilane (1%). The resin was treated with this mixture for three hours with agitation and at ambient temperature, in a proportion of 100 ml of solution per gram of resin. The peptide free in solution was recovered by filtration. The peptide was then precipitated and washed under cold conditions in diisopropyl ether and then dissolved in 20% acetic acid and lyophilized.

Folding of the Peptides of the Present Invention by Formation of Disulphide Bridges The peptide recovered after lyophilization, the synthesis crude, is in reduced form, i.e. the intrachain disulphide bridges are not formed. The formation of these covalent bonds was carried out using the redox couple cystamine/cysteamine. The synthesis crude was taken up in water into which 0.1% (v/v) TFA and 6M guanidinium chloride had been added to facilitate the dissolving thereof, at 2.0 mg/ml$^{-1}$. This solution was then added dropwise, diluted to 0.2 mg/ml$^{-1}$, to the reducing buffer composed of 100 mM Tris/HCl, pH 7.8, and 5 mM cysteamine. The cystamine (oxidant) at a final concentration of 0.5 mM was added after reaction for 45 minutes at ambient temperature. The medium is brought to pH 3.0 after 30 minutes.

The cysteamine makes it possible to reduce the thiol groups present on the peptide. In the open air, it oxidizes and allows oxidation of cysteines and therefore the folding of the peptide by formation of intrachain disulphide bridges. The cystamine added at the end of the manipulation makes it possible to complete the folding. The correct progression of the oxidation is verified by analytical chromatography, comparing the retention time of the crude and oxidized products, that of the first being longer.

The oxidation of the peptide CD4M9, exhibiting a thiol group at position 11, differs slightly from that described in the paragraph above. The folding reaction medium, composed of a 20 mM phosphate buffer containing 200 mM NaCl, adjusted to pH 7.8, is degassed with argon for a considerable amount of time and then 5 mM of cysteamine and 5 mM of cystamine are added. The peptide comprising seven free SH functions is then added and the oxidation reaction is stopped by adding acid after only 10 minutes, an amount of time sufficiently long for the folding and for the formation of the three natural disulphide bridges and sufficiently short to limit the formation of by-products corresponding to higher oxidation states.

Purification of the Peptides of the Present Invention

The peptides of the present invention were purified by reverse-phase high performance liquid chromatography on a Vydac C18 preparative column (1.0×25.0 cm). A 0-60% linear gradient of acetonitrile in a 0.1% aqueous trifluoroacetic acid solution, over 90 minutes, was used. The fractions of the major peak were analysed by analytical HPLC; the fractions exhibiting only one peak were pooled and lyophilized. The product thus obtained was analysed by mass spectrometry.

Example 2

Competition Assays by Indirect ELISA

The inhibition of the rgp120-CD4 interaction was measured by indirect ELISA (Enzyme Linked ImmunoSorbent Assay). 50 ng per well of anti-gp120 antibody, D7324, were immobilized on a 96-well plate (Maxisorb, Nunc) overnight at 4° C. After passivation with bovine serum albumin and three washes with the washing buffer (10 mM Tris, pH 7.8, 0.05% Tween 20), 15 ng of rgp120$_{HXB2}$ per well were added. Various concentrations of competitors were then added, after three washes, and also 0.4 ng of soluble CD4 per well. 100% controls containing only soluble CD4 were prepared. After overnight incubation at 4° C. and three washes, 5 ng of mouse anti-CD4 antibody L120.3 were added per well, followed by a peroxidase-coupled goat anti-mouse IgG antibody (GAMPO). The revelation was carried out by adding 3,3',5,5'-tetramethylbenzidine, a fluorescent substrate for peroxydase. The reaction was stopped after 30 minutes by adding 2M sulphuric acid. The inhibition of the rgp120-CD4 interaction was calculated by reading the absorbance A at 450 nm. Controls without competitor made it possible to determine the absorbance $A_{100\%}$ (absorbance in the absence of competitor). The percentage inhibition for each concentration of peptide of the present invention was calculated using the formula:

$$\text{percentage inhibition} = 100 \times (A_{100\%} - A)/A_{100\%}.$$

The assays were carried out in duplicate and the results were expressed as the mean of experimental duplicates.

The biological activities of the peptide CD4MO (sequence ID No. 18) derived from charybdotoxin and of the peptide CD4M3 (sequence ID No. 17) derived from scyllatoxin (sequence ID No. 2) were assayed in an indirect ELISA assay. These peptides exhibit an ability to inhibit the rgp120$_{LAI}$-soluble CD4 interaction with a 50% inhibitory concentration (or IC$_{50}$) of $4.0 \times 10^{-5}$ M and of $2.0 \times 10^{-5}$ M respectively (Table I) [4]. These values are 10 000 times higher than the $IC_{50}$ given by soluble CD4 ($IC_{50}=4.0\times10^{-9}$ M) [4].

The attached FIG. 1 groups together the results obtained in this example with the peptides of the present invention.

They are representations of the percentage attachment (% F) of the viral protein gp120$_{HXB2}$-CD4 as a function of the molar concentration (C(M)) of competitor, i.e. of peptide of the present invention. This figure shows the inhibition of the CD4-gp120$_{HXB2}$ interaction.

CD4M9 (sequence ID No. 3) was assayed by competition on ELISA. It exhibits the ability to inhibit the rgp120$_{LAI}$-soluble CD4 interaction with a 50% inhibitory concentration (or $IC_{50}$) of $4\times10^{-7}$ M (Table I), that is a 50-fold increase in the inhibition capacity compared to the peptide of the present invention CD4M3 (sequence ID No. 17). The peptide of the present invention CD4M9, in a competition ELISA assay, is also capable of inhibiting the interaction of CD4 with other recombinant gp120 proteins originating from T- and M-tropic virus: HIV-1$_{IIIB}$, HIV-1$_{MN}$, HIV-1$_{Ba-L}$, HIV-1$_{JR-FL}$, HIV-1$_{W61D}$, with a 50% inhibitory concentration ($IC_{50}$) of between 0.1 and $1.0\times10^{-6}$ M [4].

This peptide inhibits the gp120$_{HXB2}$-soluble CD4 interaction at an $IC_{50}$ of $9\times10^{-8}$ M (FIG. 1, Table I).

A mutant, CD4MV, comprising the substitution of the C-terminal sequence Gly-Pro of CD4M9 with Val, exhibits an $IC_{50}$ of $3.0\times10^{-7}$ M in the inhibition of the gp120$_{LAI}$-CD4 interaction (Table 1), which represents a slight increase in the inhibitory capacity. The mutant CD4M9Dip comprises the substitution Phe23Dip compared to CD4M9; this peptide exhibits an $IC_{50}$ of $1.0\times10^{-7}$ M in the inhibition of the gp120$_{LAI}$-CD4 interaction (Table 1), which represents a further increase in the inhibitory capacity. The mutant CD4M9T (sequence ID No. 4), comprising a thiopropionic acid as a substitution for the N-terminal Cys amino acid, exhibits an $IC_{50}$ of $3.0\times10^{-8}$ M in the inhibition of the gp120$_{LAI}$-CD4 interaction (FIG. 1; the IC$_{50}$ in the gp120$_{HXB2}$ interaction is 1.1×10$^{-8}$ M, Table 1), which represents a close to 10-fold increase in the inhibitory capacity compared to CD4M9.

The following mutants all exhibit a thiopropionic (TPA) and valine (Val or Ile) residue in the N- and C-terminal position, respectively, and were all tested with gp120, derived from the T-tropic viruses HIV-1$_{HXB2}$ and HIV-1$_{LAI}$.

The peptide of the present invention CD4M27 (sequence ID No. 6) comprises the mutations Arg5Phe (to remove a non-essential arginine and to protect the disulphide bridge 6-24) and Gly27Val, and deletion of the C-terminal proline residue (to give better stability to the the β-structure). It exhibits an increase in the ability to inhibit the CD4-gp120$_{HXB2}$ binding, IC$_{50}$ of 7×10$^{-9}$ M (FIG. 1, Table I). The peptides CD4M27 A, B and C are obtained, respectively, by a mutation Gly21Ser(a), Ser22His(b) and Ser22Asn(c) starting with the peptide CD4M27. They exhibit an inhibitory capacity comparable to that of the peptide CD4M27.

The peptide of the present invention CD4M32 (sequence ID No. 12), compared to CD4M9T, comprises deletion of the C-terminal proline residue, the mutation Gly27Val and the mutation of Phe23 to diphenylalanine (Dip): the mutation Phe23Dip adds a hydrophobic extension to the side chain of the Phe23, so as to increase the interaction with the hydrophobic cavity of the viral protein gp120. CD4M32 exhibits an increase in the inhibition of the CD4-gp120$_{HXB2}$ binding (IC$_{50}$ of 8×10$^{-10}$ M, FIG. 1). The mutant CD4M30 (sequence ID No. 10), compared to CD4M32, comprises the mutation Arg5Phe (already introduced into CD4M27) and Ala4Gln in order to increase the solubility of the molecule. This peptide of the present invention exhibits an IC$_{50}$ of 3.0 nM, in the assays for inhibition of the CD4-gp120$_{LAI}$ interaction. The mutant CD4M33 (sequence ID No. 13) includes the mutations present in the two preceding peptides, in particular Cys1TPA, Arg5Phe, Phe23Dip, Gly27Val, deletion of a residue in the C-terminal position and, in addition, the mutation Ala4His (to increase the solubility of the molecule). These mutations have an additive effect and enable the peptide of the present invention CD4M33 to inhibit the CD4-gp120$_{HXB2}$ and CD4-gp120$_{LAI}$ interactions with an IC$_{50}$ of 1.2×10$^{-10}$ M and of 2.5×10$^{-10}$ M (FIG. 1 and Table 1), i.e. a 1000-fold increase in the ability to inhibit the CD4-gp120 binding compared to CD4M9. An additional peptide, CD4M35 (sequence ID No. 14), was synthesized with, compared to the peptide CD4M33 of the present invention, the mutations Val27Ile and Gly21(D)Asp. These mutations enable the peptide of the present invention to inhibit the CD4-gp120$_{HXB2}$ interaction with an IC$_{50}$ of 7.0×10$^{-11}$ M (FIG. 1, Table 1).

Two other peptides, K15 (sequence ID No. 15) and K16 (sequence ID No. 16), were synthesized: they comprise the substitutions Gln7Val, Leu8Gln and Lys11His, compared to the peptide CD4M33 of the present invention, and a Lys residue at position 15 or 16, respectively. A fluorescein fluorescent group was then attached covalently to the side chain of this lysine residue, according to the protocol described in Example 1. The fluorescent K15 and K16 peptides exhibit an IC$_{50}$ of 5.0×10$^{-8}$ M and 6.0×10$^{-9}$ M in the inhibition of the gp120$_{LAI}$-CD4 interaction, in which the affinity for the viral protein gp120 is not modified by labelling.

In conclusion, the present invention provides a family of peptides which represent powerful inhibitors of the CD4-gp120 interaction.

TABLE 1

50% inhibitory concentration (IC$_{50}$) of the CD4 mimetic peptides in the interaction of soluble recombinant CD4 for the viral envelope protein gp120$_{LAI}$ and gp120$_{HXB2}$. The standard deviation for each value is less than 30%.

| Name | Sequence Idno | IC$_{50}$ (gp120$_{LAI}$) | IC$_{50}$ (gp120$_{HXB2}$) |
|---|---|---|---|
| CD4M0 | 18 | 40 μM | — |
| CD4M3 | 17 | 20 μM | — |
| CD4M9 | 3 | 400 nM | 90 nM |
| CD4M9V | — | 300 nM | — |
| CD4M9T | 4 | 30 nM | 11 nM |
| CD4M9Dip | — | 100 nM | — |
| CD4M27 | 6 | 10 nM | 7 nM |
| CD4M30 | 10 | 3.0 nM | — |
| CD4M32 | 12 | 2.0 nM | 800 pM |
| CD4M33 | 13 | 250 pM | 120 pM |
| CD4M35 | 14 | — | 70 pM |
| K15FR | 15 | 50 nM | — |
| K16FR | 16 | 6 nM | — |

Example 3

Surface Plasmon Resonance Experiments

The surface plasmon resonance experiments were carried out with a Biacore 2000 system (Biacore, Uppsala, Sweden). The peptides to be tested were coupled to biotin (as described previously) and then immobilized on a chip to which streptavidin had been previously attached.

The streptavidin was immobilized on the chip as follows: the surface of the chip was first activated by injection of 50 μL of coupling agent provided by the constructor and able to form amide bonds: N-ethyl-N'-(dimethylaminopropyl)carbodiimide (EDC)/N-hydroxy-succinimide (NHS), 50/50; then, 20 μL of streptavidin, 0.2 mg.mL$^{-1}$ in 10 mM sodium acetate, pH 4.5, were injected at 5 μL.min$^{-1}$, followed by neutralization of the activated carboxylic groups with 2×20 μL of 1.0 M ethanolamine, pH 8.5. The biotinylated molecules were then injected (10 μL.min$^{-1}$ in a 10 mM Hepes buffer containing 0.3 M NaCl, pH 7.4) onto three of the four lanes of the chip. On the first lane, CD4M9 (10$^{-7}$ M) was immobilized up to an RU (resonance unit) value of 100; the second lane was left unused (control); the third lane was covered with soluble CD4 (10$^{-7}$ M) up to a value of 450 RU; on the fourth lane, CD4M33 (10$^{-7}$ M) was immobilized at a value of 100 RU. For each analysis, several concentrations of various gp120s (strains HXB2, BAL and JRFL) were injected, at a rate of 50 μL.min$^{-1}$ at 25° C., for an association time of 4 min. The chip is then rinsed with a running buffer, 10 mM Hepes containing 150 mM NaCl, 3.4 mM EDTA and 0.05% P20, pH 7.4, in order to analyse the dissociation phase. After each experiment, the chip is regenerated with 25 μL of 1.0 M formic acid. The dissociation constants are calculated from the kinetic constants determined by the Bia-evaluation 3.0 software.

Example 4

Antiviral Activity of the CD4 Mimetics

The handling of the infectious material was carried out in an L3-type high security laboratory. In order to be as close as possible to the physiopathological conditions, the study was carried out using primary cultures of human peripheral blood mononuclear cells (PBMCs). In all the experiments, the effects of the new molecules were compared to those of AZT.

Isolation, Culture and Activation of the Cells Culture Media

The medium A is composed of RPMI 1640 cell culture medium (Life Technologies) supplemented with 10% of foetal calf serum (SVF, Roche Product) heat-decomplemented at +56° C. for 30 min of 2 mM of L-glutamine (Roche Product) and of a 100 µg/ml solution of three antibiotics (penicillin, streptomycin, neomycin; PSN, Life Technologies). The medium B consists of medium A supplemented with 20 UI/ml of recombinant human IL-2 (Roche Product).

Isolation and Activation of the PBMCs

The PBMCs are separated from the other represented elements of the blood by ficoll (MSL 2000, Eurobio) gradient centrifiguation: 30 ml of blood, from a healthy donor, diluted by a third are deposited onto a 20 ml ficoll cushion. After centrifugation for 20 min at 850 g, the ring of PBMCs is removed and then washed twice with RPMI 1640, after centrifugation at 750 g for 10 min and at 400 g for 5 min. The PBMCs are then activated for 48 h with 1 µg/ml of phytohaemagglutinin-P (PHA-P; Difco Laboratories). The PBMCs are cultured at +37° C., in an atmosphere saturated with humidity, under 5% $CO_2$. At the end of the 48 hours of mitogenic activation, they are cultured in medium B. Throughout the culturing, the culture supernatants are sampled, and the culture media are renewed every three or four days. At each renewal of the culture media, the cell viability is evaluated by microscopic observation.

Evaluation of the Antiretroviral Activity of the Molecules

The compounds of the present invention CD4M30, CD4M33 and CD4M35 were solubilized in sterile water for injectable preparation (Aguettant), aliquoted, and then stored at −20° C. The compound SAH-CD4 (soluble CD4 coupled to human serum albumin provided by Aventis (Vitry-sur-Seine)) was stored at −80° C. until it was used. The solutions and the dilutions were then prepared extemporaneously in medium A. The PBMCs were pretreated with the compounds for 1 hour and then infected with the reference isolate having lymphocytic tropism, HIV-$1_{LAI}$, or with the clinical isolate HIV-$1_{LEN}$.

The biological characteristics of this isolate are: rapid/high, scyncitia inducing (SI), ×4: it is therefore preferentially able to infect lymphocytes. The viral stock was constituted by amplifying this strain in vitro, using umbilical cord blood mononuclear cells (UCBMCs) pre-activated with 1 µg/ml of PHA-P and cultured in medium B. In order to remove the soluble factors such as cytokines, the culture supernatants were ultracentrifuged at 360 000 g for 5 min, and the pellets were resuspended in RPMI 1640. The viral stock thus constituted was then titred using PHA-P-activated PBMCs. The $TCID_{50}$ (50% Tissue Culture Infectious Dose) was calculated using the Kärber formula. The PBMCs were infected with various viral doses, 10-100 $TCID_{50}$, of the strain HIV-$1_{LAI}$ and with 50 $TCID_{50}$ of the strain HIV-$1_{LEN}$ (multiplicity of infection m.o.i.=0.001).

Assaying the Viral Replication in the Culture Supernatants

The viral replication was measured, on day 7 of the culture, by assaying the reverse transcriptase activity in the culture supernatants using the RetroSys (registered trade mark) assay kit according to the recommendations of the company Innovagen.

Analysis of the results and determination of the 50% effective doses

The 50% effective doses ($ED_{50}$) are calculated using the "Dose-effects analysis with microcomputers" software developed by J. Chou & T. C. Chou.

Example 5

Protocol for Producing the Recombinant Viral Protein gp120

The fragment encoding the viral protein gp120 (amino acid V12 to R481) was amplified by PCR in the plasmid HIVIIIB/HXB2R, using two primers making it possible to generate a fragment containing the BamHI (upstream of the KpnI site of the viral protein gp120) and PstI (downstream of the stop codon added to the end of the sequence of the viral protein gp120) sites. The BamHI/PstI fragment thus obtained was cloned into the Bluescript vector (pBS, Stratagene), producing the plasmid pBSm1. The sequence encoding the N-terminal end of the viral protein gp120 (T1 to G11), and also that encoding the signal peptide of the ecdysteroid glycosyltransferase of the Autographa californica baculovirus, were inserted between the BamHI and KpnI sites of pBSm1, producing pBSm2.

The BamHI-PstI fragment of pBSm2 was then inserted between the BglII-PstI sites of the transfer vector p119P of the baculovirus P10. Sf9 insect cells were cotransfected with the purified viral DNA of the modified baculovirus AcSLP10 and the DNA of the recombinant vector p119P gp120. The recombinant viruses are purified by a standard method.

Sf9 scla cells (line adapted to growth without serum, deposited with the collection of the Pasteur Institute) are maintained in a spinner in serum-free medium. These cells ($5×10^5$ cells/mL) are then infected with the recombinant viruses at a multiplicity of infection of 1 PFU (plaque-forming unit) per cell and incubated at 28° C. After infection for six days, the cells are centrifuged (500 g) and the wild-type gp120 viral protein is concentrated and directly purified from the culture supernatant by affinity chromatography on a column of bromoacetylated Sepharose coupled to the anti-gp120 antibody D7324.

Example 6

Attachment of the Viral Envelope

In order to more thoroughly characterize its biological activity, the peptide of the present invention CD4M33 (sequence ID No. 13) was labelled with biotin and with the fluorescein fluorescent probe as described in Example 1, on the Lys-11 positioned on the surface opposite to the active surface of the peptide of the present invention CD4M33. Its activity remains unchanged in ELISA assays (FIG. 2).

Figure 2:
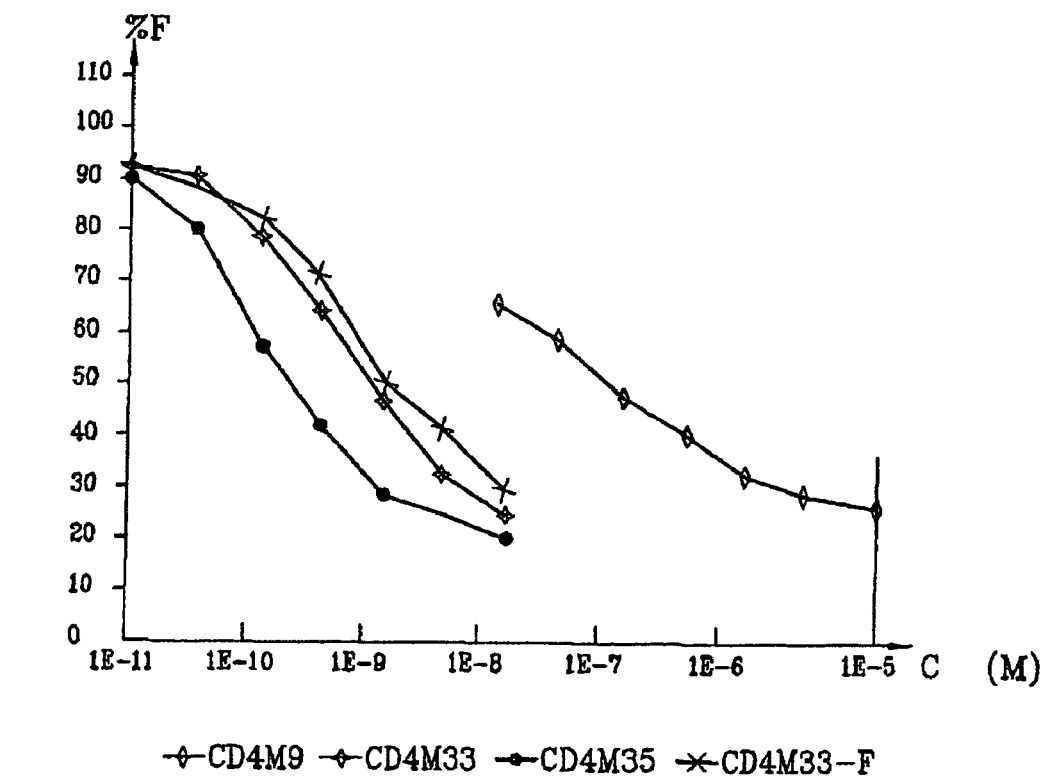
FIG. 2: Curve of inhibition of the binding of CD4 to the viral protein gp120, with the labelled peptide CD4M33-fluorescein, CD4M33-F, obtained by competition ELISA. The curves for the peptides CD4M9 (sequence ID No. 3), CD4M33 (sequence ID No. 13) and CD4M35 (sequence ID No. 14) are also represented for comparison. The experimental data are given as percentage binding (% F) as a function of the peptide concentration.

FIG. 2 groups together the results obtained in this example. These are curves showing the evolution of the percentage attachment (% F) of peptides of the present invention with the viral protein $gp120_{HXB2}$ as a function of the molar concentration of these peptides (C(M)).

These results show that the peptide CD4M33 can incorporate a labelling group without its biological activity being altered.

Figure 3:
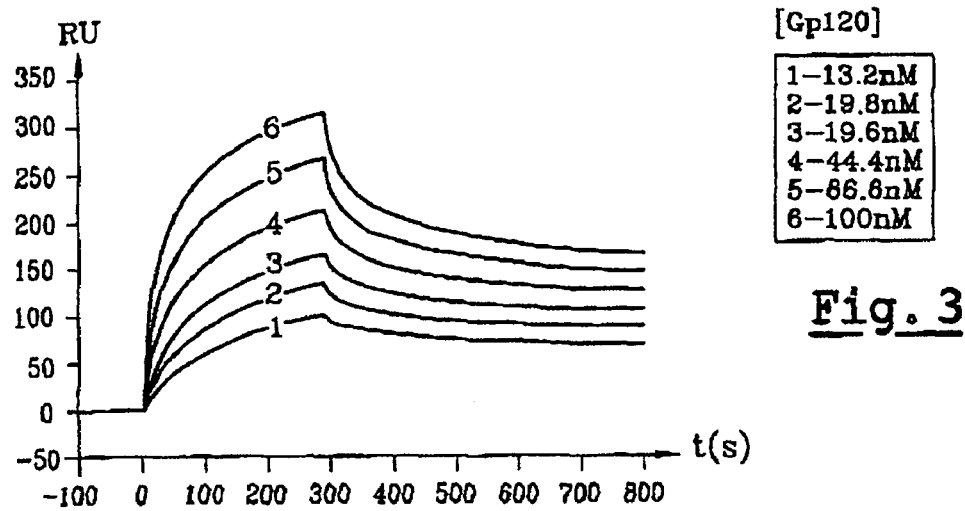
FIG. 3: Curves of interaction of the recombinant viral protein gp120-HXB2 with the peptide CD4M33 (sequence ID No. 13) attached to the surface of a chip of a surface plasmon resonance instrument. The association (0-300 s) and dissociation (300-800 s) curves were recorded after injection of the viral protein gp120 at the concentrations 13.2(1), 19.8(2), 29.6(3), 44.4(4), 66.6(5) and 100(6) nM. The data are given in resonance units (RU) as a function of time (t) in seconds.

In order to obtain a first evaluation of the affinity of the peptide of the present invention CD4M33 for the viral protein gp120, an analysis of biospecific interactions (described in Example 3), based on detection by surface plasmon resonance, was used. In this technique, the biotinylated peptide CD4M33 of the present invention (prepared as in Example 1) was specifically attached to the carboxylated dextran matrix of a chip onto which streptavidin had been pregrafted. Solutions, of various recombinant gp120 proteins ($gp120_{HXB2}$, $gp120_{BAL}$ and $gp120_{JRFL}$) were then injected onto this matrix and a signal indicating a specific and high affinity association was then detected. FIG. 3 shows the evolution of the plasmon resonance signal as a function of time, after interaction of the $gp120_{HXB2}$ protein (at different concentrations) with the peptide CD4M33 of the present invention.

After non-linear regression of the association and dissociation curves obtained, a dissociation constant $K_D$ of $2.4 \times 10^{-9}$ M is obtained for the viral protein $gp120_{HXB2}$, of $7.4 \times 10^9$ M is obtained for the viral protein $gp120_{BAL}$ and of $8.5 \times 10^{-9}$ M, is obtained for the viral protein $gp120_{JRFL}$. These values are comparable to the value of $K_D = 1.9 \times 10^{-8}$ M, reported in the literature [34] for the CD4-gp120 interaction. The same technique, based on detection by surface plasmon resonance, was also used to verify whether the peptide of the present invention CD4M33 could attach the viral envelope in its native form. To do this, a suspension of viral particles inactivated with aldrithiol-2 [35] was injected onto the same chip, grafted with the antibodies 48d and CG10. A signal for specific and high affinity interaction was then clearly detected, when the suspension was incubated with the peptide of the present invention CD4M33, but not when the viral suspension was incubated with the peptide CD4M9, which is much less active, or in the absence of peptide (FIG. 4).

Figure 4:
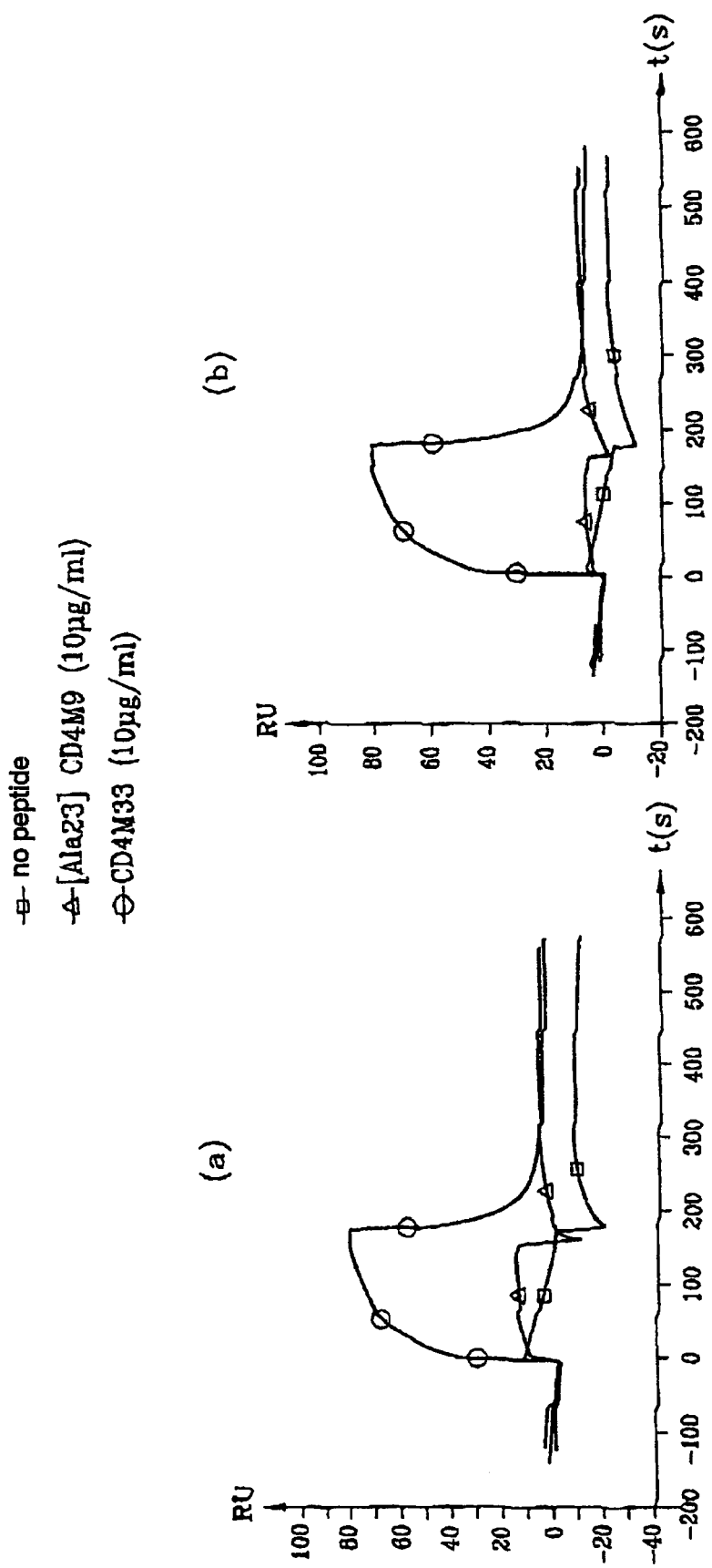
FIGS. 4(a) and (b): Curve of interaction of HIV-1, inactivated with AT-2 [34], with the antibody 48d [11] (a) and CG10 [35] (b), attached to the surface of a chip of a surface plasmon resonance instrument in the presence of the peptide CD4M33 (10 µg/ml), in the presence of an inactive peptide (Ala23) CD4M9 (Phe23 replaced with Ala in the peptide sequence of CD4M9) (10 µg/ml) and in the absence of peptide. The association (0-180 s) and dissociation (180-600 s) curves were recorded after injection of HIV-1, which had been pre-incubated with the peptides at 20° C. for 1 h. The data are given in resonance units (RU) as a function of time (t) in seconds.

FIG. 4 shows that the presence of the peptide CD4M33 is essential for the interaction of the viral envelope with the viral envelope-specific antibodies 48d and CG10, and that HIV-1 does not attach to the antibodies in its absence: this is an indirect demonstration of the attachment of the peptide CD4M33 to the viral envelope of HIV-1.

These experiments demonstrate that the peptide of the present invention CD4M33, labelled or unlabelled, has an ability to attach the HIV viral envelope both in its isolated and purified recombinant form and in its native form present at the surface of the virus.

Example 7

Inhibition of the Infection with HIV-1

In order to evaluate the antiviral capacity of the peptides of the present invention, the inventors carried out experiments consisting of infection, with the $HIV-1_{LAI}$ virus and with the chemical isolate $HIV-1_{LEN}$, of primary cultures of human peripheral blood mononuclear cells (PBMCs). In all the experiments, the effects of the new molecules were compared to those of AZT. The $HIV-1_{LAI}$ virus was added at various viral doses (10-100 $TCID_{50}$, Table 2) in the presence of varying concentrations of CD4M30, CD4M33, CD4M35 and SAH-CD4. The $HIV-1_{LEN}$ virus was added at $TCID_{50}$ (Table 4) in the presence of CD4M33. CD4 mimetic toxicity tests were also carried out on the same cells.

a. Toxicity of the CD4 mimetics. At the doses tested, none of the compounds, AZT, SAH-CD4 or anti-CD4 mimetics, decreased the viability of the PHA-P-activated PBMCs.

b. Anti-$HIV-1_{LAI}$ Activity of the CD4 Mimetics b.1. Replication of the strain $HIV-1_{LAI}$ in PBMCs. The strain $HIV-1_{LAI}$ replicates at high level in PHA-P-activated PBMCs. The peak of viral replication is on day 7 of the culture, and the effects of the peptides CD4M30, CDM33 and CD4M35 were quantified at this time post-infection.

b.2. Effects of AZT on the replication of the strain $HIV-1_{LAI}$ in PBMCs. AZT strongly inhibits the replication of the strain $HIV-1_{LAI}$ in PHA-P-activated PBMCs (Table 2). The $ED_{50}$ is equal to 3-14 nM.

b.3. Effects of the compound SAH-CD4 on the replication of the strain $HIV-1_{LAI}$ in PBMCs. The antiretroviral activity of the compound SAH-CD4 with respect to the PBMCs activated with PHA-P and infected with the strain $HIV-1_{LAI}$ results in an 85±15% inhibition of the viral replication at the concentration of 2.5 µM.

b.4. Effects of the CD4 mimetics on the replication of the strain $HIV-1_{LAI}$ in PBMCs. The peptides of the present invention CD4M30, CD4M33 and CD4M35 demonstrated antiretroviral activity (Table 3) in the cultures of PBMCs activated with PHA-P and infected with strain $HIV-1_{LAI}$. The compound CD4M33 is the most antiviral of the three at the various viral doses tested. Its activity is less than that of AZT: $ED_{50}$=100-500 nM vs. AZT: $ED_{50}$=3 nM (Table 3 below), but it is at least 1 base 10 logarithm greater than that of the CD4 receptor derivative SAH-CD4.

Figure 5A:
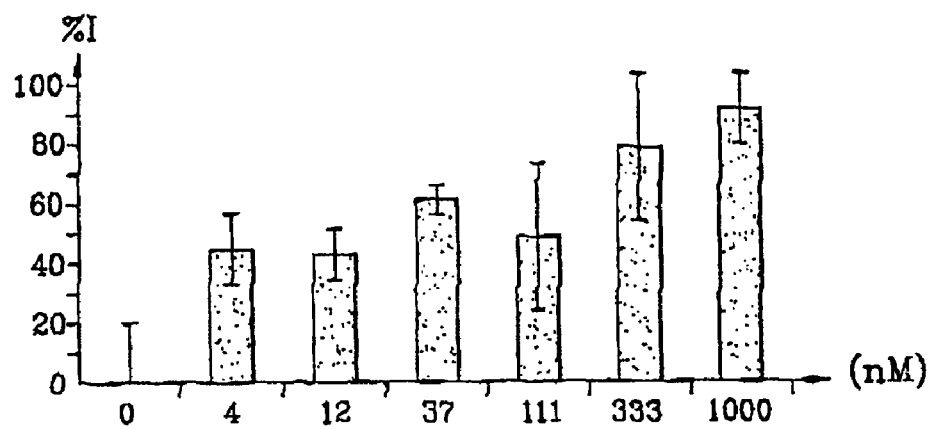
FIGS. 5(A)-(C): Effects of the peptides CD4M30 (sequence ID No. 10) (FIG. 4A), CD4M33 (sequence ID No. 13) (FIG. 4B) and CD4M35 (sequence ID No. 14) (FIG. 4C) on the replication of the HIV-1$_{LAI}$ strain in PBMCs activated with PHA-P. The data are represented as percentage inhibition (% I) of the reverse transcriptase (RT) activity in the culture supernatants as a function of the peptide concentration in nM.
Figure 5B:
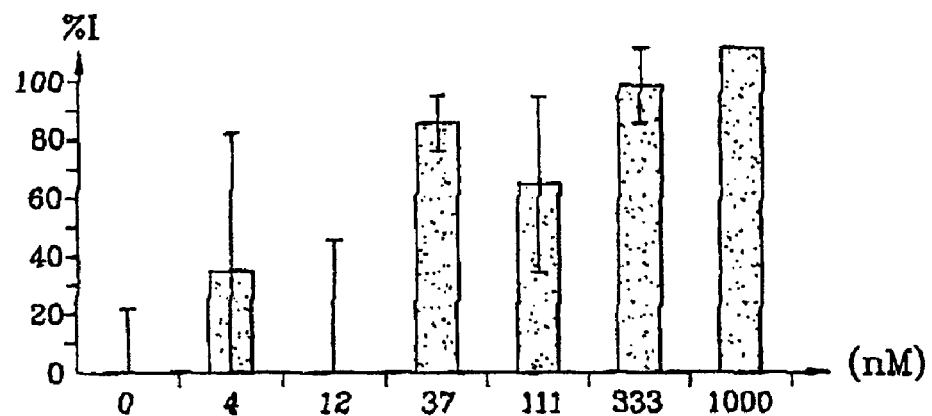
Figure 5C:
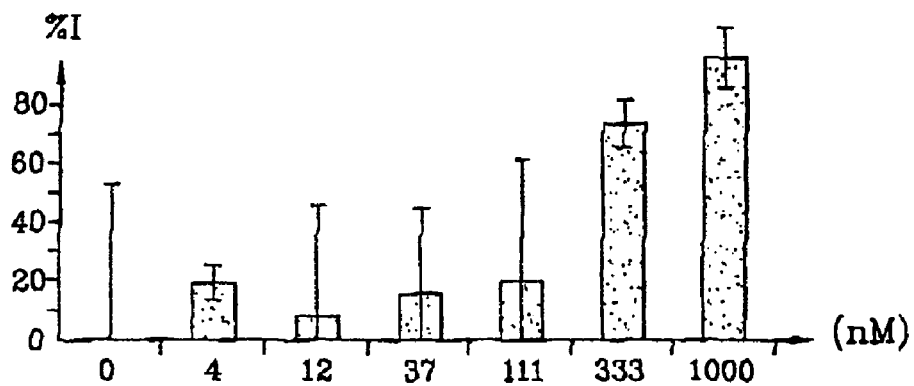

FIGS. 5A-C group together the results obtained: percentage inhibition (% I) as a function of the concentration of peptide in nM.

c. Antiretroviral Activity of the Compound CD4M33 with Respect to the Clinical Isolate $HIV-1_{LEN}$ c1. Effects of AZT on the Replication of the Isolate $HIV-1_{LEN}$ in PBMCs AZT strongly inhibits the replication of the strain $HIV-1_{LEN}$ in the PBMCs activated with PHA-P and infected with the isolate $HIV-1_{LEN}$, with an $ED_{50}$ equal to 2.2 nM (Table 4). The degree of inhibition is identical to that observed with respect to the reference strain having lymphocytic tropism, $HIV-1_{LAI}$.

c2. Effects of the Mimetic CD4M33 on the Replication of the Clinical Isolate $HIV-1_{LEN}$ in PBMCs The retroviral activity of the mimetic CD4M33 with respect to the PBMCs activated with PHA-P and infected with the isolate $HIV-1_{LEN}$ relates in a dose-dependent decrease in the viral replication and an $ED_{50}$ equal to 367 nM (Table 4). The mimetic CD4M33 therefore conserves a significant anti-HIV-1 activity, even though it is found to be slightly lower compared to that observed with the strain $HIV-1_{LAI}$.

These experiments demonstrate that these peptides of the present invention are capable of inhibiting the infection of the cells, even at high viral doses, with $ED_{50}$ values of 900-35 nM (Table 3 below). The peptide of the present invention CD4M33 is the most antiviral and its $ED_{50}$ is approximately 100 nM for the standard viral doses for infection (FIG. 4a-c, Table 3 below).

In addition, the peptide CD4M33 possesses an antiretroviral activity which is greater by 1 base 10 logarithm than that observed with another CD4 receptor derivative, SAH-CD4, and especially showed a significant anti-HIV activity with respect to a clinical isolate (Table 4).

In conclusion, the peptide of the present invention CD4M33, which is capable of attaching to the recombinant viral protein gp120 with a Kd of 2.4-8.0 nM (surface plasmon resonance experiments) and of inhibiting the interaction between the CD4-gp120 recombinant proteins in ELISA, with an $IC_{50}$ of 120-250 pM, also exhibits the ability to inhibit this interaction in primary cultures of human cells, to inhibit the initial step of entry, and therefore to block the infection even of an HIV-1 clinical isolate.

TABLE 2

Effect of AZT on the replication of the strain HIV-$1_{LAI}$ in PHA-P-activated PBMCs. The results are expressed as percentage inhibition ± standard deviation:

| AZT (nM) | % inhibition |
|---|---|
| 1 | 39 + 10% |
| 10 | 59 + 28% |
| 100 | 87 ± 18% |
| 100 | 100 ± 0% |
| 10,000 | 100 ± 0% |

TABLE 3

50% effective doses ($ED_{50}$) of the peptides of the present invention and of AZT in cultures of human peripheral blood mononuclear cells (PMBCs) activated with phytohaemogglutinin-P (PHA-P) and infected with strain HIV-$1_{LAI}$ at various infectious doses ($TCID_{50}$: 50% Tissue Culture Infectious Dose):

| | $ED_{50}$ (nM) | | |
|---|---|---|---|
| Sequences | 100 $TCID_{50}$ | 50 $TCID_{50}$ | 10 $TCID_{50}$ |
| CD4M30 | 894 | 235 | 253 |
| CD4M33 | 534 | 133 | 118 |
| CD4M35 | 154 | 428 | 266 |
| AZT | 14 | 3 | 5 |

TABLE 4

Effect of AZT and of mimetic CD4M33 on the replication of the clinical isolate HIV-$1_{LEN}$ in cultures of human peripheral blood mononuclear cells (PBMCs) activated with phytohaemogglutinin-P (PHA-P). The cells were infected with 50 $TCID_{50}$ of virus:

| HIV-$1_{LEN}$ | AZT | CD4M33 |
|---|---|---|
| $ED_{50}$ (nM) | 2.2 | 367 |
| $ED_{70}$ (nM) | 4.8 | 542 |
| $ED_{90}$ (nM) | 16.5 | 1006 |

Example 8

Exposure of Antigenic Sites of the Envelope

Figure 6A:
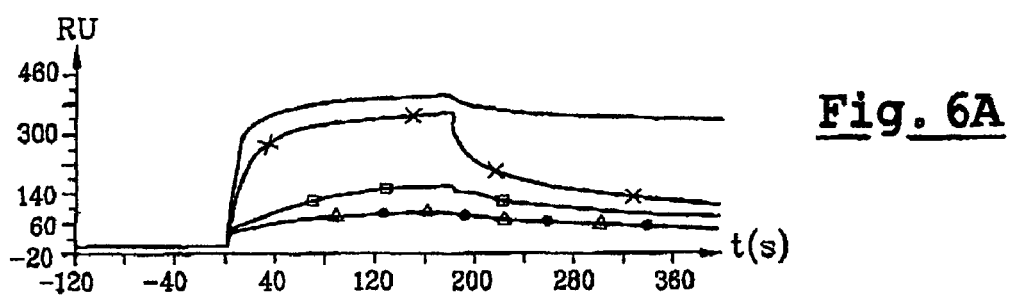
FIGS. 6(A) and (B): Effect of the presence of soluble CD4 and of the peptides of the present invention on the interaction of the recombinant viral protein gp120$_{HXB2}$ with the antibodies CG10 (A) and 48d (B), attached to the surface of a chip of a surface plasmon resonance instrument. The association (0-180 s) and dissociation (180-400, 180-450 s) curves are given for the viral protein gp120 alone and the viral protein gp120 in the presence of CD4M27 (1.5 equivalents, sequence ID No. 6), of CD4M9 (1.5 equivalents), of the inactive mutant (Ala23)CD4M9 (1.5 equivalents) and of soluble CD4 (1.5 equivalents). The data are given as resonance units (RU) as a function of time (t) in seconds.
Figure 6B:
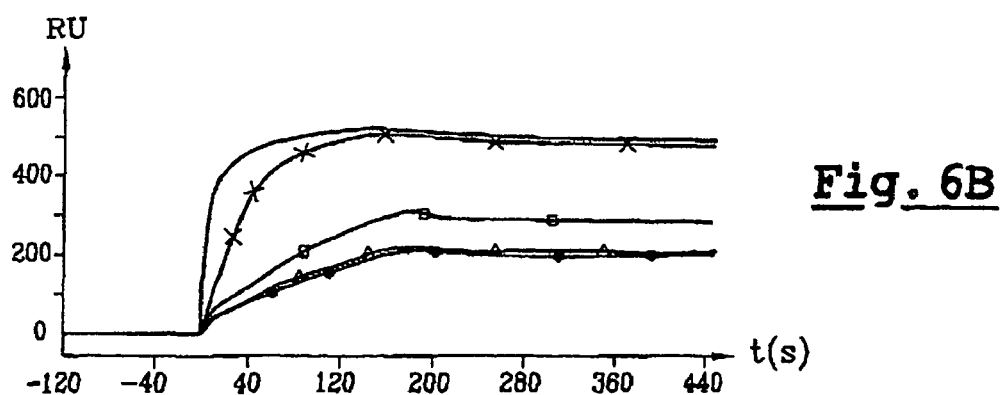

In order to evaluate the ability of the peptide of the present invention CD4M33 to induce conformational variations in the gp120 protein, characterized by the exposure of epitopes sensitive to neutralizing antibodies, the interaction of such human antibodies, 48d and CG10, with the HIV envelope in the presence of CD4M33 and, by comparison, of recombinant CD4, was undertaken using the surface plasmon resonance technique. The antibodies 48d and CG10 were covalently attached to the surface of the chips (biochip), and the solutions of gp120, in the absence of CD4 and in the presence of an excess of CD4 and of CD4M33, were injected. When CD4M33 is added to the viral protein gp120$_{HXB2}$, with a 1.5-fold and 20-fold molar excess, the viral protein exhibits a strong interaction with the antibodies (FIGS. 6a-b); on the other hand, in its absence (and in the absence of soluble CD4), the envelope protein interacts very weakly with the antibodies (FIG. 6a-b). In addition, the effect of adding CD4M33 on the increase in the affinity of interaction of the viral protein gp120 for the antibodies is comparable to that which is obtained by adding equivalent amounts of soluble CD4.

The inventors also carried out similar plasmon resonance experiments, directly using HIV-1, strain HXB2. FIG. 4 shows the results obtained in these experiments and demonstrates the evolution of the plasmon resonance signal as a function of time after interaction of a suspension of HIV-$1_{HXB2}$ viral particles with a chip exhibiting the immobilized antibodies 48d and CG10: the HIV-1 interacts with the antibodies only after incubation with peptide CD4M33 of the present invention and, on the other hand, in its absence or, in the presence of the inactive peptide [Ala23]CD4M9, the interaction is virtually zero.

The surface plasmon resonance technique therefore made it possible to demonstrate that binding of CD4M33 to the envelope protein gp120 is capable of inducing a modification of the viral protein, which subsequently preferentially exposes certain molecular surfaces to the neutralizing antibodies (17b, CG10), isolated from individuals infected with HIV-1 [11], [12], [13].

The exposure of these cryptic epitopes, induced by the peptide CD4M33 of the present invention, is effective both in the protein of the envelope in recombinant form and in the envelope of the virions. In addition, in view of the recent experiments which show that the gp120 protein complexed with CD4 may be a molecular form capable of inducing the formation of neutralizing antibodies [31, 32, 33], the CD4M33-gp120 complex therefore represents a very advantageous candidate as an immunogen for inducing neutralizing antibodies, in particular in a vaccine application.

CD4M33 has the property of unmasking epitopes of the viral protein gp120, as does soluble CD4, with the advantage that it will not be able to induce an immune response against CD4 and that, in addition, due to its small size, it will enable even more favourable access to the unmasked epitopes of the viral protein gp120.

Example 9

Synthesis of a Chromatographic Support for Purifying the HIV Viral Envelope

To evaluate the possibility of using the CD4 mimetic peptide of the present invention as an immobilized ligand for functionalizing a chromatographic matrix for purifying the viral protein gp120, a hydrophilic polymeric support, Sepharose 4B (Pharmacia, Uppsala, Sweden) was functionalized with one of our CD4 mimetics and then used to attach the viral protein gp120 directly from the viral protein culture medium. In order to avoid using conditions which were too drastic during the elution of the gp120 protein from the support and to therefore limit the possibilities of denaturation, a ligand with lower affinity for the viral protein gp120 was chosen. It is CD4M9, which, by ELISA, exhibits an affinity ($IC_{50}$) for the viral protein gp120 of between 0.1 μM and 1.0 μM, depending on the HIV-1 isolate. CD4M9 was modified on the position Lys11, already used in the preceding labellings, so as to include an additional thiol group (described in Example 1), which was then used for its covalent immobilization on the Sepharase 4B support, as described below.

The resin EAH Sepharose (trade mark) (marketed by Pharmacia Biotech), comprising 7 to 12 μmol of primary amine functions per ml of dry resin, is functionalized with a maleimide group. For this, 12 ml of resin pre-equilibrated in 24 ml of water are treated for 12 h with 1.05 mg of reagent sulpho-SMCC (3-sulpho-M-hydroxysuccinimide ester of 4-(N-maleimidoethyl)-cyclohexane-1-carboxylic acid (Sigma)), maintaining the pH at approximately 4.5. The expected degree of substitution is 200 nmol of maleimide function per ml of dry resin. The excess reagent is then removed by successive washes with 100 mM Tris-HCl, 500 mM NaCl, pH 8.0, and then with a 100 mM sodium acetate buffer containing 500 nM NaCl, pH 4.0. The remaining free amine functions are then acetylated by two treatments with a 1% acetic anhydride solution. 3.8 mg of thiolated peptide CD4M9 are added to the resin functionalized with maleimide. The reaction is agitated at 4° C. for 12 hours. The resin is then washed and equilibrated with the using buffer, 20 mM sodium phosphate, 100 mM NaCl, pH 7.4. A 6.0 ml chromatographic column was prepared with this matrix which contained approximately 0.1 mg/ml of immobilized peptide according to the present invention CD4M9. This column was then loaded with the gp120 culture medium and the viral protein retained on the column was then eluted from the column with 0.5 M acetic acid treatment. The fractions eluted with the acetic acid were then analysed by SDS-PAGE and then lyophilized. The analysis of these fractions demonstrated that they contained the viral protein gp120.

Figure 8:
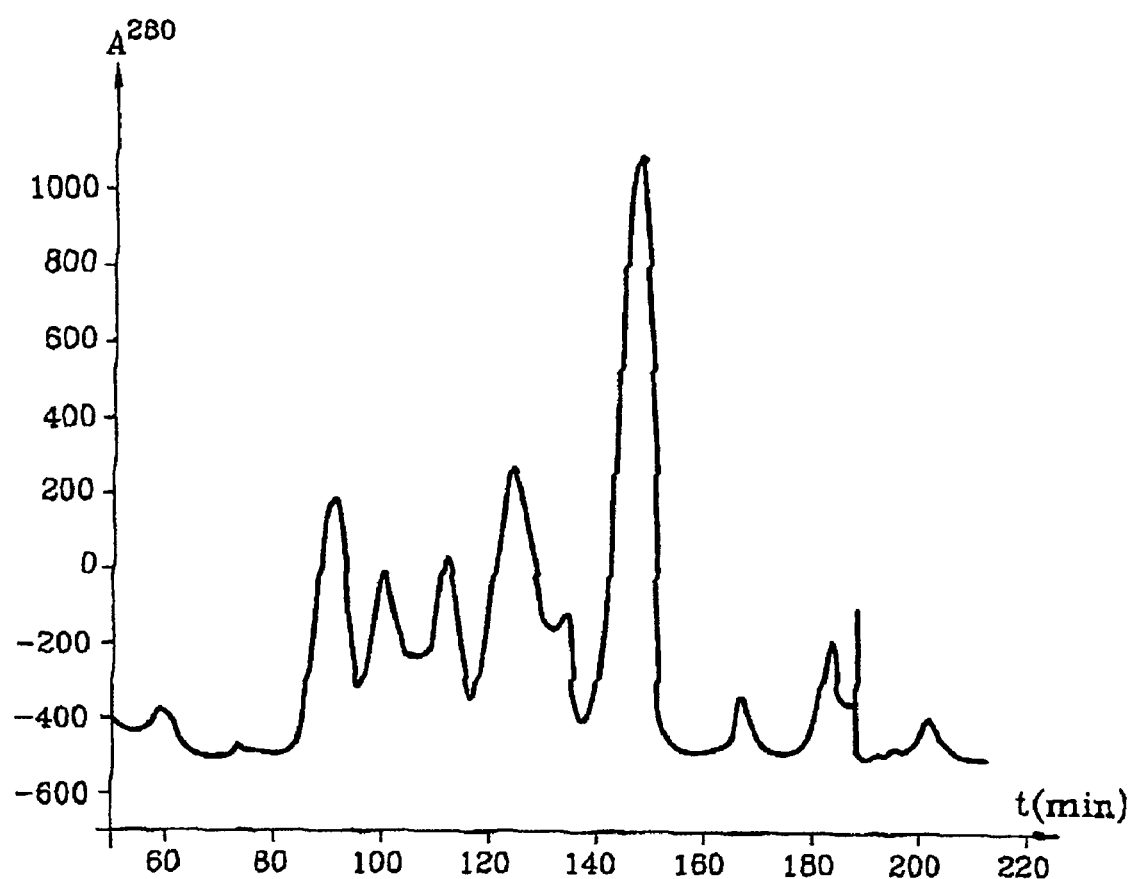
FIG. 8: Chromatographic profile of the purification of the recombinant protein gp120$_{HXB2}$ on a Sepharose 4B column (1.2×4 cm) funcionalized with the peptide of the present invention CD4M9 (sequence ID No. 3). The data are given as absorbance at 280 nm as a function of time (min), after addition of 0.5 M acetic acid.

FIG. 8 is a graph representing the chromatographic profile obtained in this example: absorbance at 280 nm (A280) as a function of time in minutes (t(min)).

The chromatographic profile in FIG. 8 shows several envelope protein elution peaks. The inventors think that the various peaks represent the viral protein gp120 at different degrees of denaturation caused by the acetic acid used in the elution from the column.

Example 10

Screening

Molecules of the present invention were labelled with fluorescein or biotin without modifying the affinity for binding to the viral protein gp120.

In this example, a labelling is carried out with fluorescent lanthanide metals or radioactive isotopes, without altering the binding activity of the peptides of the present invention with respect to the viral protein gp120. These labelled peptides are used as tracers, in experiments consisting of screening, by competition, the interaction of these peptides with the viral protein gp120.

In a first experiment, the viral protein gp120 is immobilized in 96-well microplates and the peptide CD4M33, labelled with the lanthanide europium (III), is brought into contact with this protein under conditions which allow the interaction between the CD4M33 peptide and the gp120 protein. Signal measurements (for example time-resolved fluorescence measurements) make it possible to quantify the ability of the screened molecules to displace the labelled peptides.

In a second experiment, the peptide CD4M33 is labelled with fluorescein and bound to the viral protein gp120, and is protected by measurements of fluorescence polarization in solution, in miniaturized systems.

These two systems, used to screen molecules capable of inhibiting the CD4-gp120 interaction, are not limiting. The molecules detected by this screening represents inhibitors of the CD4-gp120 interaction, and therefore potentially inhibitors of the viral infection.

The techniques for implementation used in this example are described in the literature, in particular in documents [37, 38, 39 and 40].

REFERENCES

[1] Kwong, P. D., Wyatt, R., Robinson, J., Sweet, R. W., Sodroski, J., Hendrickson, W. A. (1998) *Nature* 393, 648-659

[2] Sweet, R. W., Truneh, A., Hendrickson, W. A. (1991) *Curr. Opin. Biotechnol.* 2, 622-633.

[3] Ryu, S. E., Trueh, A., Sweet, R. W., Hendrickson, W. A. (1994) *Structure* 2, 59-74.

[4] Vita, C., Drakopoulou, E., Vizzavona, J., Rochette, S., Martin, L., Ménez, A., Roumestand, C., Yang, Y. S., Ylistagui, L., Benjouad, A., Gluckman, J. C. 1999, *Proc. Natl. Acad. Sci. USA*, 96, 13091-13096

[5] Feng, Y., Broder, C. C., Kennedy, P. E., Berger, E. A. (1996) *Science* 272, 872-877.

[6] Choe, H., Farzan, M., Sun, Y., Sullivan, N., Rollins, B., Ponath, P. D., Wu, L., Mackay, C. R., LaRosa, G., Newman, W., Gerard, N., Gerard, C., Sodroski, J. (1996) *Cell* 85, 1135-1148.

[7] Dragic, T., Litwin, V., Allaway, G. P., Martin, S. R., Huang, Y., Nagashima, K. A., Cayanan, C., Maddon, P. J., Koup, R. A., Moore, J. P., Paxton, W. A. (1996) *Nature* 381, 667-673.

[8] Alkhatib, G., Combadiere. C., Broder, C. C., Feng, Y., Kennedy, P. E., Murphy, P. M., Berger, E. A. (1996) *Science* 272, 1955-1958.

[9] Wu, L., Gerard, N. P., Wyatt, R., Choe, H., Parolin, C., Ruffing, A., Borsetti, A., Cardoso, A. A., Desjardin, E., Newman, W., Gerard, C., Sodroski, J. (1996) Nature 384, 179-183.

[10] Trkola, A., Dragic, T., Arthos, J., Binley, J. M., Olson, W. C., Allaway, G. P., Cheng-Mayer, C., Robinson, J., Maddon, P. J., Moore, J. P. (1996) *Nature* 384, 184-187.

[11] Thali, M., Moore, J. P., Furman,. C., McArthur, C., Ho, D. D., Robinson, J., Sodroski, J. (1993) *J. Virol.* 67, 3978-3988.

[12] Wyatt, R., Moore, J., Accola, M., Desjardin, E., Robinson, J., Sodroski, J. (1995) *J. Virol.* 69, 5723-5733.

[13] Moore, J., Sodroski J. (1996) *J. Virol.* 70, 1863-1872.

[14] Chen S., Chrusciel, R. A., Nakanishi H., Raktabutr, A., Jonhson, M. E., Sato, A., Weiner, D., Hoxie, J., Sagarovi, H. U., Greene, M. I., Kahn, M. (1992), *Proc. Natl. Acad. Sci., USA,* 89, 5872-5876.

[15] Zhang, X., Gaubin, M., Briant, L., Srikantan, V., Murali, R., Saragoui, U., Weiner, D., Devaux, C., Autiero, M., Piatier-Tonneau, D., Greene, M. I. (1997), *Nature Biotechnol.,* 15, 150-154

[16] Moore, J. P., Sweet, R. W. (1993), *Perspect. Drug Disc. Design* 1, 235-250.

[17] Allaway G P, Davis-Bruno K L, Beaudry G A, Garcia E B, Wong E L, Ryder A M, Hasel K W, Gauduin M C, Koup R A, McDougal J S, et al. (1995) *AIDS Res Hum Retroviruses.* 11, 533-539

[18] Ono, M., Wada, Y., Wu, Y., Nemori, R., Jinbo, Y., Wang, H., Lo, K. M., Yamaguchi, N., Brunkhorst, B., Otomo, H., Wesolowski, J., Way, J. C., Itoh, I., Gillies, S., Chen, L. B. (1997) *Nat. Biotechnol.* 15, 343-348.

[19] Ojwang, J. O., Buckheit, R. W., Pommier, Y., Mazumder, A., De Vreese, K., Este, J. A., Reymen, D., Pallansch, L. A., Lackman-Smith, C., Wallace, T. L., et al. (1995) *Antimicrob. Agents Chemother.* 39, 2426-2435.

[20] Rusconi, S., Moonis, M., Merrill, D. P., Pallai, P. V., Neidhardt, E. A., Singh, S. K., Willis, K. J., Osburne, M. S., Profy, A. T., Jenson, J. C., Hirsch, M. S. (1996) *Antimicrob. Agents Chemother.* 40, 234-236.

[21] De Clercq, E. (1998) Pure Appl. Chem. 70, 567-577.

[22] Yahi, N., Fantini, J., Baghdiguian, S., Mabrouk, K., Tamalet, C., Rochat, H., Van Rietschoten, J., Sabatier, J. M. (1995) *Proc. Natl. Acad. Sci. USA* 92, 4867-4871.

[23] De Clercq, E., Yamamoto, N., Pauwels, R., Balzarini, J., Witvrouw, M., De Vreese, K., Debyser, Z., Rosenwirth, B., Peichl, P., Datema, R., Thornton, D., Skerlj, R., Gaul, F., Padmanabhan, S., Bridger, G., Henson, G., Abrams, M. (1994) *Antimicrob. Agents Chemother.* 38, 668-674.

[24] Howard, O. M., Oppenheim, J. J., Hollingshead, M. G., Covey, J. M., Bigelow, J., McCormack, J. J., Buckheit, R. W. Jr, Clanton, D. J., Turpin, J. A., Rice, W. G. (1998) *J. Med. Chem.* 41, 2184-2193.

[25] Tamamura, H., Murakami, T. Masuda, M., Otaka, A., Takada, W., Ibuka, T., Nakashima, H., Waki, M., Matsumoto A., Yamamoto, N. et al. (1994), *Biochem. Biophys. Res. Commun,* 205, 1729-1735.

[26] Tamamura, H., Omagari, A., Oishi, S., Kanamoto, T., Yamamoto, N., Peiper, S. C., Nakasima, H., Otaka, A., Fujii, N. (2000) *Bioorg. Med. Chem. Lett.* 10, 2633-2637.

[27] Baba, M., Nishimura, O., Kanzaki, N., Okamoto, M., Sawada, H., Iizawa, Y., Shiraishi, M., Aramaki, Y., Okonogi, K., Ogawa, Y., Meguro, K., Fujino, M. (1999) *Proc. Natl. Acad. Sci. USA* 96, 5698-5703.

[28] Wild, C., Dubay, J. W., Greenwell, T., Baird, T. Jr, Oas, T. G., McDanal, C., Hunter, E., Matthews, T. (1994) Proc. Natl. Acad. Sci. USA 91, 12676-80.

[29] Rimsky, L. T., Shugars, D. C., Matthews, T. J. (1998) *J. Virol.* 72, 986-993.

[30] Chun, T. W, Fauci, A. S. (1999) *Proc. Natl. Acad. Sci. USA* 96, 10958-10961.

[31] LaCasse R. A., Follis K. E., Trahey, M., Scarborough, J. D., Littman, D. R., Nunberg, J. H. (1999) *Science* 283, 357-362.

[32] Devico A, Silver A, Thronton A M, Sarngadharan M G, Pal R. (1996) *Virology* 218, 258-63.

[33] Fouts T R, Tuskan R, Godfrey K, Reitz M, Hone D, Lewis G K, DeVico A L. (2000) *J Virol.* 74, 11427-36

[34] Rossio, J. L., Esser, M. T., Suryanarayana, K., Schneider, D. K., Bess, J. W. Jr, Vasquez, G. M., Wiltrout, T. A., Chertova, E., Grimes, M. K., Sattentau, Q., Arthur, L. O., Henderson, L. E., Lifson, J. D. (1998) *J. Virol.* 72, 7992-8001.

[35] Lee, S., Peden, K. Dimitrov, D. S., Broder, C. C., Manischewitz, J., Denisova, G., Gershoni, J. M., Golding, H. (1997) *J. Virol.* 71, 6037-6043.

[36] Wu, M., Myszka, D. G., Tendian, S. W., Brouillette, C. G., Sweet, R. W., Chaiken, I. M., Heudrickson, W. A. (1996), Proc. *Natl. Acad. Sci. USA* 93, 15030-15035.

[37] McMahon J. B., Beutler, J. A., O'Keefe, B. R., Goodrum, C. B., Myers, M. A., Boyd, M. R. (2000) *J. Biomol. Screen* 5, 169-176.

[38] Sportsman, J. R., Leytes, L. J. (2000) *Drug Discov, Today* 1, 27-32.

[39] Pernelle C., et al., *Biochemistry,* 1993, 32(43), 11682-7.

[40] Mathis G.; *Clin. Chem.,* 1993, 39(9), 1953-9.

---

SEQUENCE LISTING

```
<160> NUMBER OF SEQ ID NOS: 19

<210> SEQ ID NO 1
<211> LENGTH: 16
<212> TYPE: PRT
<213> ORGANISM: Homo sapiens

<400> SEQUENCE: 1

Gln Ile Lys Ile Leu Gly Asn Gln Gly Ser Phe Leu Thr Lys Gly Pro
1               5                   10                  15

<210> SEQ ID NO 2
<211> LENGTH: 31
<212> TYPE: PRT
<213> ORGANISM: Scorpion

<400> SEQUENCE: 2

Ala Phe Cys Asn Leu Arg Met Cys Gln Leu Ser Cys Arg Ser Leu Gly
1               5                   10                  15

Leu Leu Gly Lys Cys Ile Gly Asp Lys Cys Glu Cys Val Lys His
            20                  25                  30

<210> SEQ ID NO 3
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 3

Cys Asn Leu Ala Arg Cys Gln Leu Arg Cys Lys Ser Leu Gly Leu Leu
1               5                   10                  15

Gly Lys Cys Ala Gly Ser Phe Cys Ala Cys Gly Pro
            20                  25

<210> SEQ ID NO 4
```

```
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid

<400> SEQUENCE: 4

Xaa Asn Leu Ala Arg Cys Gln Leu Arg Cys Lys Ser Leu Gly Leu Leu
1               5                   10                  15

Gly Lys Cys Ala Gly Ser Phe Cys Ala Cys Gly Pro
            20                  25

<210> SEQ ID NO 5
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid
<220> FEATURE:
<221> NAME/KEY: MOD_RES
<222> LOCATION: (23)..(23)
<223> OTHER INFORMATION: bi-phenylalanine or naphtylalanine

<400> SEQUENCE: 5

Xaa Asn Leu His Phe Cys Val Gln Arg Cys His Ser Leu Gly Leu Leu
1               5                   10                  15

Gly Lys Cys Ala Gly Ser Xaa Cys Ala Cys Val
            20                  25

<210> SEQ ID NO 6
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid

<400> SEQUENCE: 6

Xaa Asn Leu Ala Phe Cys Gln Leu Arg Cys Lys Ser Leu Gly Leu Leu
1               5                   10                  15

Gly Lys Cys Ala Gly Ser Phe Cys Ala Cys Val
            20                  25

<210> SEQ ID NO 7
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid

<400> SEQUENCE: 7

Xaa Asn Leu Ala Phe Cys Gln Leu Arg Cys Lys Ser Leu Gly Leu Leu
1               5                   10                  15
```

Gly Lys Cys Ala Ser Ser Phe Cys Ala Cys Val
            20                  25

<210> SEQ ID NO 8
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid

<400> SEQUENCE: 8

Xaa Asn Leu Ala Phe Cys Gln Leu Arg Cys Lys Ser Leu Gly Leu Leu
1               5                   10                  15

Gly Lys Cys Ala Gly His Phe Cys Ala Cys Val
            20                  25

<210> SEQ ID NO 9
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid

<400> SEQUENCE: 9

Xaa Asn Leu Ala Phe Cys Gln Leu Arg Cys Lys Ser Leu Gly Leu Leu
1               5                   10                  15

Gly Lys Cys Ala Gly Asn Phe Cys Ala Cys Val
            20                  25

<210> SEQ ID NO 10
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid
<220> FEATURE:
<221> NAME/KEY: MOD_RES
<222> LOCATION: (23)..(23)
<223> OTHER INFORMATION: bi-phenylalanine or naphtylalanine

<400> SEQUENCE: 10

Xaa Asn Leu Gln Phe Cys Gln Leu Arg Cys Lys Ser Leu Gly Leu Leu
1               5                   10                  15

Gly Lys Cys Ala Gly Ser Xaa Cys Ala Cys Val
            20                  25

<210> SEQ ID NO 11
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid
<220> FEATURE:

<221> NAME/KEY: MOD_RES
<222> LOCATION: (23)..(23)
<223> OTHER INFORMATION: bi-phenylalanine or naphtylalanine

<400> SEQUENCE: 11

Xaa Asn Leu His Phe Cys Gln Leu Arg Cys Lys Ser Leu Gly Leu Leu
1               5                   10                  15

Gly Lys Cys Gln Gly Ser Xaa Cys Thr Cys Val
            20                  25

<210> SEQ ID NO 12
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid
<220> FEATURE:
<221> NAME/KEY: MOD_RES
<222> LOCATION: (23)..(23)
<223> OTHER INFORMATION: bi-phenylalanine or naphtylalanine

<400> SEQUENCE: 12

Xaa Asn Leu Ala Arg Cys Gln Leu Arg Cys Lys Ser Leu Gly Leu Leu
1               5                   10                  15

Gly Lys Cys Ala Gly Ser Xaa Cys Ala Cys Val
            20                  25

<210> SEQ ID NO 13
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid
<220> FEATURE:
<221> NAME/KEY: MOD_RES
<222> LOCATION: (23)..(23)
<223> OTHER INFORMATION: bi-phenylalanine or naphtylalanine

<400> SEQUENCE: 13

Xaa Asn Leu His Phe Cys Gln Leu Arg Cys Lys Ser Leu Gly Leu Leu
1               5                   10                  15

Gly Lys Cys Ala Gly Ser Xaa Cys Ala Cys Val
            20                  25

<210> SEQ ID NO 14
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid
<220> FEATURE:
<221> NAME/KEY: MOD_RES
<222> LOCATION: (21)..(21)
<223> OTHER INFORMATION: D-isomer of aspartic acid
<220> FEATURE:
<221> NAME/KEY: MOD_RES
<222> LOCATION: (23)..(23)
<223> OTHER INFORMATION: bi-phenylalanine or naphtylalanine

<400> SEQUENCE: 14

Xaa Asn Leu His Phe Cys Gln Leu Arg Cys Lys Ser Leu Gly Leu Leu
1               5                   10                  15

Gly Lys Cys Ala Xaa Ser Xaa Cys Ala Cys Ile
            20                  25

<210> SEQ ID NO 15
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid

<400> SEQUENCE: 15

Xaa Asn Leu His Phe Cys Val Gln Arg Cys His Ser Leu Gly Lys Leu
1               5                   10                  15

Gly Lys Cys Ala Gly Ser Phe Cys Ala Cys Val
            20                  25

<210> SEQ ID NO 16
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: thiopropionic acid

<400> SEQUENCE: 16

Xaa Asn Leu His Phe Cys Val Gln Arg Cys His Ser Leu Gly Leu Lys
1               5                   10                  15

Gly Lys Cys Ala Gly Ser Phe Cys Ala Cys Val
            20                  25

<210> SEQ ID NO 17
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 17

Cys Asn Leu Ala Arg Cys Gln Leu Ser Cys Lys Ser Leu Gly Leu Lys
1               5                   10                  15

Gly Gly Cys Gln Gly Ser Phe Cys Thr Cys Gly
            20                  25

<210> SEQ ID NO 18
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 18

Val Ser Cys Thr Thr Ser Lys Glu Cys Trp Ser Val Cys Gln Arg Leu
1               5                   10                  15

His Asn Thr Ser Lys Gly Gly Cys Gln Gly Ser Phe Cys Thr Cys Gly

-continued

```
                 20                  25                  30
Pro

<210> SEQ ID NO 19
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 19

Glx Phe Thr Asn Val Ser Cys Thr Thr Ser Lys Glu Cys Trp Ser Val
1               5                   10                  15

Cys Gln Arg Leu His Asn Thr Ser Arg Gly Lys Cys Met Asn Lys Lys
            20                  25                  30

Cys Arg Cys Tyr Ser
            35
```

The invention claimed is:

1. A peptide comprising the following sequence:

TPA-Asn-Leu-(Ala or Gln or His)-(Arg or Phe)-Cys-Xaa$^c$-Xaa$^d$-Arg-Cys-(His or Lys)-Ser-Leu-Gly-Xaa$^h$-(Leu or Lys)-Gly-Lys-Cys-(Ala or Gln)-(Gly or (D)Asp or Ser)-(Ser or His or Asn)-Xaa$^j$-Cys-(Thr or Ala)-Cys-Xaa$^k$-NH$_2$ (SEQ ID NO: 20)

wherein TPA is thiopropionic acid;

Xaa$^c$ is an amino acid selected from the group consisting of Gln and Val;

Xaa$^d$ is an amino acid selected from the group consisting of Gln and Leu;

Xaa$^h$ is an amino acid selected from the group consisting of Leu and Lys;

Xaa$^j$ is selected from the group consisting of β-naphthylalanine, phenylalanine, and diphenylalanine; and Xaa$^k$ is an amino acid selected from the group consisting of Gly, Ile, and Val, wherein said Xaa$^k$ amino acid is optionally linked to a Pro amino acid.

2. The peptide according to claim 1, wherein said Xaa$^k$ amino acid is linked to Pro.

3. The peptide according to claim 2, wherein Lys is present at amino acid position 11.

4. The peptide according to claim 3, wherein said sequence is selected from the group consisting of SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14.

5. The peptide according to claim 2, wherein His is present at amino acid position 11.

6. The peptide according to claim 5, wherein said sequence is selected from the group consisting of SEQ ID NO: 5, SEQ ID NO: 15, and SEQ ID NO: 16.

7. A method for producing the peptide according to claim 1, wherein said method comprises solid-phase chemical synthesis of the peptide.

8. A composition comprising a complex of the peptide according to claim 1 and an envelope protein of a virus.

9. The composition according to claim 8, wherein the virus is a human immunodeficiency virus (HIV).

10. A process for preparing a composition comprising a complex of the peptide according to claim 1 and an envelope protein of a virus, wherein said process comprises combining the peptide with the envelope protein of the virus to form the complex of the composition.

11. The process according to claim 10, wherein the virus is a human immunodeficiency virus (HIV).

12. A composition comprising the peptide according to claim 1 and a physiologically acceptable medium.

13. A process for preparing a composition comprising the peptide according to claim 1 and a physiologically acceptable medium, wherein said process comprises combining the peptide with the physiologically acceptable medium.

14. A method for detecting a viral envelope gp120 protein, or an analogue thereof, of a retroviral immunodeficiency virus, wherein said method comprises:

Contacting the peptide according to claim 1 with the viral envelope gp120 protein, or an analogue thereof, of the immunodeficiency virus to form a complex; and detecting the complex.

15. The method according to claim 14, wherein the immunodeficiency virus is a human immunodeficiency virus (HIV).

16. A method of purifying a viral envelope protein gp120, or an analogue thereof, of a retroviral immunodeficiency virus wherein said method comprises:

Immobilizing the peptide according to claim 1 on a chromatographic matrix to form an immobilized peptide; and contacting the viral envelope protein gp120, or an analogue thereof, with the immobilized peptide to form a complex.

17. A method of screening a viral envelope gp120 protein, or an analogue thereof, of a retroviral immunodeficiency virus wherein said method comprises:

Labeling the peptide according to claim 1 with a marker to form a labeled peptide; and contacting the viral envelope gp120 protein, or an analogue thereof, with the labeled peptide to form a labeled peptide/envelope protein complex; and detecting the labeled complex.

* * * * *